United States Patent [19]

Junge et al.

[11] Patent Number: 4,968,679
[45] Date of Patent: Nov. 6, 1990

[54] 8-SUBSTITUTED 2-AMINOTETRALINS

[75] Inventors: Bodo Junge, Wuppertal; Bernd Richter, Bergisch Gladbach; Thomas Glaser, Roesrath; Jörg Traber, Lohmar, all of Fed. Rep. of Germany; George S. Allen, Nashville, Tenn.

[73] Assignee: Bayer Aktiengesellschaft, Leverkusen, Fed. Rep. of Germany

[21] Appl. No.: 354,950

[22] Filed: May 22, 1989

Related U.S. Application Data

[62] Division of Ser. No. 132,372, Dec. 15, 1987, Pat. No. 4,873,262.

[30] Foreign Application Priority Data

Dec. 22, 1986 [DE] Fed. Rep. of Germany ....... 3643899
Jun. 15, 1987 [DE] Fed. Rep. of Germany ....... 3719924

[51] Int. Cl.$^5$ ............... A61K 31/135; C07C 211/38
[52] U.S. Cl. ............... 514/222.2; 514/224.5; 514/255; 514/278; 514/319; 514/372; 514/373; 514/408; 514/416; 514/417; 514/510; 514/577; 514/595; 514/596; 514/603; 514/605; 514/615; 514/649; 514/651; 514/654; 514/657; 514/663; 544/14; 544/33; 544/398; 544/402; 546/16; 546/205; 546/206; 548/206; 548/207; 548/473; 548/482; 548/578; 558/418; 558/426; 560/10; 560/28; 560/45; 560/48; 560/163; 564/47; 564/48; 564/56; 564/86; 564/92; 564/99; 564/163; 564/168; 564/352; 564/378; 564/387; 564/428
[58] Field of Search ............... 544/14, 33, 348, 402; 546/16, 205, 206; 548/206, 207, 473, 482, 578; 558/418, 426; 560/10, 28, 48, 45, 163; 564/47, 48, 56, 86, 92, 99, 163, 168, 352, 378, 387, 428; 514/222.2, 224.5, 255, 278, 319, 372, 373, 408, 416, 417, 577, 510, 595, 596, 603, 605, 619, 649, 651, 654, 657, 663

[56] References Cited

U.S. PATENT DOCUMENTS 4,510,157  4/1985  Asselin et al. ....................... 514/411

FOREIGN PATENT DOCUMENTS 0041488  12/1981  European Pat. Off. .

Primary Examiner—Richard L. Raymond
Attorney, Agent, or Firm—Sprung Horn Kramer & Woods

[57] ABSTRACT

New 8-substituted 2-aminotetralins can be prepared from the corresponding aminotetralins or tetralones. They can be used in medicaments.

8 Claims, No Drawings

8-SUBSTITUTED 2-AMINOTETRALINS

This is a division, of application Ser. No. 132,372, filed Dec. 15, 1987, now U.S. Pat. No. 4,873,262.

The invention relates to 8-substituted 2-aminotetralins, a process for the preparation thereof, and the use thereof in medicaments.

It is known from EP-A1 41,488 that 8-hydroxy-2-alkylaminotetralins or 8-amino-2-dialkylaminotetralins act on the central nervous system.

New 8-substituted 2-aminotetralins of the general formula (I)

in which $R^1$ represents halogen, cyano or represents a group of the formula $-NR^4R^5$, $-COR^6$, $-(CH_2)_a-X$, $-O-(CH_2)_a-X$ or $-CH=CH-(CH_2)_b-X$, wherein $R^4$ and $R^5$ are identical or different and denote hydrogen or a group of the formula $-COR^7$ or $-SO_2R^8$, where $R^7$ represents hydrogen, or represents an $-NHR^9$ group, or represents alkoxy, or represents aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, $R^8$ represents cycloalkyl, or represents alkyl which may be substituted by cyano, halogen, trifluoromethyl, trifluoromethoxy or alkyloxycarbonyl, or represents aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or represents an $-NR^{10}R^{11}$ group, wherein $R^{10}$ and $R^{11}$ are identical or different and denote hydrogen, alkyl, aryl or aralkyl, and $R^9$ represents hydrogen, or represents cycloalkyl, or represents alkyl which is optionally substituted by cyano, halogen, trifluoromethyl or trifluoromethoxy, or represents aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, $R^6$ denotes hydrogen, hydroxyl, amino, alkoxy, aryloxy or aralkoxy, a denotes a number 1 to 10, b denotes a number 0 to 8, and X denotes a group of the formula $-NR^{12}R^{13}$, $-COR^{14}$, $-SO_2R^{15}$ or $-OR^{16}$, wherein $R^{12}$ and $R^{13}$ are identical or different and represent hydrogen, alkyl, aryl or aralkyl, where the aryl radicals may be substituted by halogen, cyano, alkyl, alkoxy or trifluoromethyl, or represent a group of the formula $-COR^{14}$, $-SO_2R^{15}$ or $-(CH_2)_c-NR^{12}R^{13}$, $R^{14}$ denotes hydrogen, or denotes an $-NHR^{17}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, $R^{15}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or denotes an $-NR^{10}R^{11}$ group, where $R^{10}$ and $R^{11}$ have the abovementioned meaning, $R^{16}$ denotes hydrogen, alkyl, aryl, aralkyl, or a group of the formula $-CONR^{10}R^{11}$, $R^{17}$ denotes hydrogen, or denotes cycloalkyl, or denotes alkyl which is optionally substituted by cyano, halogen, trifluoromethyl or trifluoromethoxy, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, and c denotes a number 1 to 8, or where $R^{12}$ and $R^{13}$, together with the nitrogen atom, form a ring from the series comprising -continued

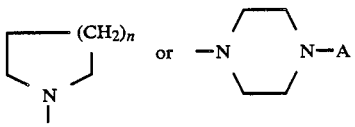

wherein n denotes a number 1 or 2, and

A represents hydrogen or cycloalkyl, or represents alkyl which may be substituted by halogen, hydroxyl, amino, alkylamino, dialkylamino, carbamoyl or sulphamoyl, or represents aryl, heteroaryl, aralkyl, alkoxycarbonyl, alkylsulphonyl, phenylsulphonyl, tolylsulphonyl, benzylsulphonyl, formyl, carbamoyl or sulphamoyl, $R^2$ represents hydrogen or alkyl, and $R^3$ represents alkyl, but where $R^1$ does not denote $NH_2$ when $R^2$ and $R^3$ denote propyl, and the salts thereof, have now been found.

Surprisingly, the substances according to the invention exhibit a superior action on the central nervous system and can be used for therapeutic treatment of humans and animals.

The substances according to the invention have several asymmetrical carbon atoms and can thus exist in various stereochemical forms.

The invention relates to the individual isomers and to mixtures thereof. The following isomeric forms of the substituted basic 2-aminotetralins may be mentioned as examples:

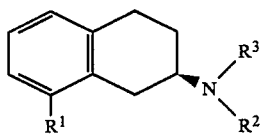

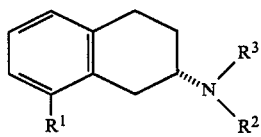

The substituted basic 2-aminotetralins according to the invention may also exist in the form of their salts. In general, salts with inorganic or organic acids may be mentioned here.

In the context of the present invention, physiologically acceptable salts are preferred. Physiologically acceptable salts of the substituted basic 2-aminotetralins may be salts of the substances according to the invention with mineral acid, carboxylic acids or sulphonic acids. Particularly preferred salts are those, for example, with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, oxalic acid, malonic acid, succinic acid, maleic acid, fumaric acid, malic acid, tartaric acid, citric acid or benzoic acid.

In the context of the present invention, the substituents generally have the following meaning:

In general, alkyl represents a branched hydrocarbon radical having 1 to 12 carbon atoms. Lower alkyl having 1 to about 6 carbon atoms is preferred. Examples which may be mentioned are methyl, ethyl, propyl, isopropyl, butyl, isobutyl, pentyl, isopentyl, hexyl, isohexyl, heptyl, isoheptyl, octyl and isooctyl.

In general, alkenyl represents a straight-chain or branched hydrocarbon radical having 2 to 12 carbon atoms and one or more, preferably one or two, double bonds. The lower alkyl radical having 2 to about 6 carbon atoms and one double bond is preferred. An alkenyl radical having 2 to 4 carbon atoms and one double bond is particularly preferred. Examples which may be mentioned are allyl, propenyl, isopropenyl, butenyl, isobutenyl, pentenyl, isopentenyl, hexenyl, isohexenyl, heptenyl, isoheptenyl, octenyl and isooctenyl.

In general, cycloalkyl represents a cyclic hydrocarbon radical having 5 to 8 carbon atoms. The cyclopentane and the cyclohexane ring is preferred. Examples which may be mentioned are cyclopentyl, cyclohexyl, cycloheptyl and cyclooctyl.

In general, aryl represents an aromatic radical having 6 to about 12 carbon atoms. Preferred aryl radicals are phenyl, naphthyl or biphenyl.

In general, aralkyl represents an aryl radical, having 7 to 14 carbon atoms, which is bonded via an alkylene chain. Aralkyl radicals having 1 to 6 carbon atoms in the aliphatic part and 6 to 12 carbon atoms in the aromatic part are preferred. Examples which may be mentioned are the following aralkyl radicals: benzyl, naphthylmethyl, phenethyl and phenylpropyl.

In general, alkoxy represents a straight-chain or branched hydrocarbon radical, having 1 to 12 carbon atoms, which is bonded via an oxygen atom. Lower alkoxy having 1 to about 6 carbon atoms is preferred. An alkoxy radical having 1 to 4 carbon atoms is particularly preferred. Examples which may be mentioned are methoxy, ethoxy, propoxy, isopropoxy, butoxy, isobutoxy, pentoxy, isopentoxy, hexoxy, isohexoxy, heptoxy, isoheptoxy, octoxy or isooctoxy.

In general, aryloxy represents an aromatic radical, having 6 to about 12 carbon atoms, which is bonded via an oxygen atom. Preferred aryloxy radicals are phenoxy or naphthyloxy.

In general, aralkoxy represents an aralkyl radical having 7 to 14 carbon atoms, the alkylene chain being bonded via an oxygen atom. Aralkoxy radicals having 1 to 6 carbon atoms in the aliphatic part and 6 to 12 carbon atoms in the aromatic part are preferred. Examples which may be mentioned are the following aralkoxy radicals: benzyloxy, naphthylmethoxy, phenethoxy and phenylpropoxy.

In general, alkylthio represents a straight-chain or branched hydrocarbon radical, having 1 to 12 carbon atoms, which is bonded via a sulphur atom. Lower alkylthio having 1 to about 6 carbon atoms is preferred. An alkylthio radical having 1 to 4 carbon atoms is particularly preferred. Examples which may be mentioned are methylthio, ethylthio, propylthio, isopropylthio, butylthio, isobutylthio, pentylthio, isopentylthio, hexylthio, isohexylthio, heptylthio, isoheptylthio, octylthio or isooctylthio.

In general, acyl represents phenyl or straight-chain or branched lower alkyl, having 1 to about 6 carbon atoms, which are bonded via a carbonyl group. Phenyl, and alkyl radicals having up to 4 carbon atoms are preferred. Examples which may be mentioned are: benzoyl, acetyl, ethylcarbonyl, propylcarbonyl, isopropylcarbonyl, butylcarbonyl and isobutylcarbonyl.

Alkoxycarbonyl may be represented, for example, by the formula

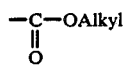

In this formula, alkyl represents a straight-chain or branched hydrocarbon radical having 1 to 12 carbon atoms. Lower alkoxycarbonyl having 1 to about 6 carbon atoms in the alkyl part is preferred. An alkoxycarbonyl having 1 to 4 carbon atoms in the alkyl part is particularly preferred. Examples which may be mentioned are the following alkoxycarbonyl radicals: methoxycarbonyl, ethoxycarbonyl, propoxycarbonyl, isopropoxycarbonyl, butoxycarbonyl or isobutoxycarbonyl.

Aryloxycarbonyl may be represented, for example, by the formula -COO-aryl. In this formula, aryl represents, in general, an aromatic radical having 6 to 12 carbon atoms. Examples which may be mentioned are: phenoxycarbonyl and naphthyloxycarbonyl.

Aralkoxycarbonyl may be represented, for example, by the formula -COO-aralkyl. In this formula, aralkyl represents, in general, an aryl radical, having 7 to 14 carbon atoms, which is bonded via an alkylene chain, aralkyl radicals having 1 to 6 carbon atoms in the aliphatic part and 6 to 12 carbon atoms in the aromatic part being preferred. Examples which may be mentioned as aralkoxycarbonyl radicals are: benzyloxycarbonyl and naphthylmethyloxycarbonyl.

In the context of the abovementioned definition, heteroaryl represents, in general, a 5- to 6-membered aromatic ring, which may contain, as heteroatoms, oxygen, sulphur and/or nitrogen and to which a further aromatic ring may be fused. 5- and 6-membered aromatic rings which contain one oxygen, one sulphur and/or up to 2 nitrogen atoms and which are optionally fused to a benzyl group are preferred. The following may be mentioned as particularly preferred heteroaryl radicals: thienyl, furyl, pyridyl, pyrimidyl, pyrazinyl, pyridazinyl, quinolyl, isoquinolyl, quinazolyl, quinoxalyl, thiazolyl, benzothiazolyl, isothiazolyl, oxazolyl, benzoxazolyl, isoxazolyl, imidazolyl, benzimidazolyl, pyrazolyl and indolyl.

In general, halogen represents fluorine, chlorine, bromine or iodine, preferably fluorine, chlorine or bromine. Halogen particularly preferably represents fluorine or chlorine.

Preferred such compounds of the general formula (I) are those in which $R^1$ represents fluorine, chlorine, bromine or cyano, or represents a group of the formula $-NR^4R^5$, $-COR^6$, $-(CH_2)_a-X$, $-O-(CH_2)_a-X$ or $-CH=CH-(CH_2)_b-X$, wherein $R^4$ and $R^5$ are identical or different and denote hydrogen, or a group of the formula $-COR^7$ or $-SO_2R^8$, where $R^7$ represents hydrogen, or represents an $-NHR^9$ group, or represents lower alkoxy, or represents phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, $R^8$ represents cyclopropyl, cyclopentyl or cyclohexyl, or represents lower alkyl which is optionally substituted by cyano, fluorine, chlorine, bromine, trifluoromethyl or lower alkoxycarbonyl, or represents phenyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, or represents a group of the formula $-NR^{10}R^{11}$, wherein $R^{10}$ and $R^{11}$ are identical or different and denote hydrogen, lower alkyl or phenyl and $R^9$ represents hydrogen, or represents lower alkyl which is optionally substituted by cyano, fluorine, chlorine or bromine, or represents phenyl, benzyl, thienyl, furyl, pyridyl, pyrimidyl, quinolyl, isoquinolyl, benzothiazolyl, benzoxazolyl, thiazolyl, oxazolyl, isooxazolyl or isothiazolyl which are optionally substituted by lower alkyl, lower alkoxy, fluorine, chlorine, bromine, trifluoromethyl, dimethylamino or diethylamino, $R^6$ denotes hydrogen, hydroxyl, amino, lower alkoxy or benzyloxy, a denotes a number 1 to 8, b denotes a number 0 to 6, and X denotes a group of the formula $-NR^{12}R^{13}$, $-COR^{14}$, $-SO_2R^{15}$ or $-OR^{16}$, where $R^{12}$ and $R^{13}$ are identical or different and represent hydrogen, lower alkyl, phenyl or benzyl, where the radicals mentioned may be substituted by fluorine, chlorine, bromine, lower alkyl, lower alkoxy or trifluoromethyl, or represent a group of the formula $-COR^{14}$, $-SO_2R^{15}$ or $-(CH_2)_c-NR^{12}R^{13}$, $R^{14}$ denotes an $-NHR^{17}$ group, or denotes lower alkyl or lower alkoxy, or denotes phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl, which are optionally substituted by lower alkyl, lower alkoxy, fluorine, chlorine, bromine, trifluoromethyl, dimethylamino or diethylamino, $R^{15}$ denotes cyclopropyl, cyclopentyl, cyclohexyl, or lower alkyl which is optionally substituted by cyano, fluorine, chlorine, bromine, trifluoromethyl or lower alkoxycarbonyl, or denotes phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl, which are optionally monosubstituted or polysubstituted by lower alkyl, lower alkoxy, fluorine, chlorine, bromine, trifluoromethyl, dimethylamino or diethylamino, the substituents being identical or different, or denotes an $-NR^{10}R^{11}$ group, where $R^{10}$ and $R^{11}$ have the abovementioned meaning, $R^{16}$ denotes hydrogen, lower alkyl, phenyl or benzyl, $R^{17}$ denotes hydrogen, or lower alkyl which is optionally substituted by cyano, fluorine, chlorine or bromine, or phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, and c denotes a number 1 to 6, or where $R^{12}$ and $R^{13}$, together with the nitrogen atom, form a ring from the series comprising wherein
n denotes a number 1 or 2,
R² represents hydrogen or lower alkyl and
R³ represents lower alkyl, but where
R¹ does not represent NH₂ when
R² and R³ denote propyl,
and the salts thereof.

Particularly preferred such compounds of the general formula (I) are those in which
R¹ represents chlorine, bromine, cyano or represents a group of the formula —NR⁴R⁵, —COR⁶, —(CH₂)$_a$—X, —O—(CH₂)$_a$—X or —CH=CH—(CH₂)$_b$—X, wherein
R⁴ and R⁵ are identical or different and denote hydrogen or a group of the formula —COR⁷ or —SO₂R⁸, wherein
R⁷ represents hydrogen, or represents an —NHR⁹ group, or represents methoxy, ethoxy, propoxy or isopropoxy, or represents phenyl, benzyl, benzyloxy, thienyl, furyl, pyridyl, pyrimidyl, quinolyl or isoquinolyl which are optionally substituted by methyl, methoxy, fluorine or chlorine,
R⁸ represents ethyl, propyl, isopropyl, butyl or isobutyl which are optionally substituted by fluorine, chlorine, methoxycarbonyl, ethoxycarbonyl, propoxycarbonyl, isopropoxycarbonyl, butoxycarbonyl or isobutoxycarbonyl, or represents phenyl, thienyl, furyl, pyridyl, pyrimidyl, quinolyl or isoquinolyl which are optionally substituted by methyl, ethyl, propyl, isopropyl, methoxy, ethoxy, propoxy or isopropoxy, or represents an —NR¹⁰R¹¹ group, wherein R¹⁰ and R¹¹ are identical or different and denote hydrogen, methyl, ethyl, propyl, isopropyl, butyl or isobutyl, and
R⁹ represents hydrogen, or represents methyl, ethyl, propyl, isopropyl, butyl, isobutyl, pentyl, isopentyl, hexyl or isohexyl which are optionally substituted by fluorine or chlorine, or represents phenyl which may be substituted by fluorine, chlorine, methyl or methoxy,
R⁶ denotes hydrogen, hydroxyl, amino, methoxy, ethoxy, propoxy, butoxy, isopropoxy or isobutoxy,
a denotes a number 1 to 6,
b denotes a number 0 to 4, and
X denotes a group of the formula —NR¹²R¹³, —COR¹⁴, —SO₂R¹⁵ or —OR¹⁶, where
R¹² and R¹³ are identical or different and represent hydrogen, methyl, ethyl, propyl, isopropyl, butyl, isobutyl, or represent phenyl which is optionally substituted by fluorine, chlorine, methyl or methoxy, or represent a —COR¹⁴, —SO₂R¹⁵ or —(CH₂)$_c$—N group, R¹⁴ denotes hydrogen, or denotes an —NHR¹⁷ group, or denotes methyl, ethyl, propyl, isopropyl, methoxy, ethoxy, propoxy, isopropoxy, or denotes phenyl, benzyl, benzyloxy, thienyl, furyl, pyridyl, pyrimidyl, quinolyl or isoquinolyl which are optionally substituted by methyl, methoxy, fluorine or chlorine,
R¹⁵ denotes methyl, ethyl, propyl, isopropyl, butyl or isobutyl which are optionally substituted by fluorine, chlorine, methoxycarbonyl, ethoxycarbonyl, propoxycarbonyl, isopropoxycarbonyl, butoxycarbonyl or isobutoxycarbonyl, or denotes phenyl, naphthyl, thienyl, furyl, pyridyl, pyrimidyl, quinolyl or isoquinolyl which are optionally monosubstituted or polysubstituted by methyl, ethyl, propyl, isopropyl methoxy, fluorine or chlorine, the substituents being identical or different, or denotes an —NR¹⁰R¹¹ group, where R¹⁰ and R¹¹ have the abovementioned meaning,
R¹⁶ denotes hydrogen, methyl, ethyl, propyl, isopropyl, phenyl or benzyl,
R¹⁷ denotes hydrogen, or denotes methyl, ethyl, propyl, isopropyl, butyl, isobutyl, pentyl, isopentyl, hexyl or isohexyl which are optionally substituted by fluorine or chlorine, or denotes phenyl which may be substituted by fluorine, chlorine, methyl or methoxy, and
c denotes a number 1 to 4,
R² represents hydrogen, methyl, ethyl, propyl or isopropyl, and
R³ represents methyl, ethyl, propyl or isopropyl, but where
R¹ does not denote NH₂ when
R² and R³ denote propyl
and the salts thereof.

Very particularly preferred such compounds of the general formula (I) are those in which
R¹ represents chlorine, bromine, cyano, or represents a group of the formula —NR⁴R⁵, —COR⁶, —(CH₂)$_a$—X, —O—(CH₂)$_a$—X or —CH=CH—(CH₂)$_b$—X, wherein
R⁴ denotes hydrogen, $R^5$ denotes a group of the formula —$COR^7$ or —$SO_2R^8$, wherein
$R^7$ represents hydrogen, or represents an —$NHR^9$ group, or represents methoxy or ethoxy,
$R^8$ represents trifluoromethyl, phenyl, tolyl, or represents an —$NR^{10}R^{11}$ group, wherein $R^{10}$ and $R^{11}$ are identical or different and denote hydrogen, methyl or ethyl, and
$R^9$ represents hydrogen, or represents methyl, ethyl, propyl, isopropyl or butyl, or represents phenyl,
$R^6$ denotes hydrogen, hydroxyl, amino, methoxy or ethoxy,
a denotes a number 1 to 4,
b denotes a number 0 to 2, and
X denotes a group of the formula —$NR^{12}R^{13}$, —$COR^4$, —$SO_2R^{15}$ or —$OR^{16}$, where
$R^{12}$ and are identical or different and represent hydrogen, methyl, ethyl or propyl, or represent a —$COR^{14}$, —$SO_2R^{15}$ or

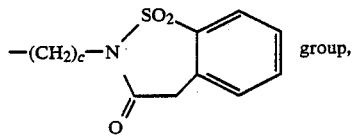

group, $R^{14}$ denotes hydrogen, or denotes an —$NHR^{14}$ group, or denotes methyl, ethyl, propyl, methoxy or ethoxy,
$R^{15}$ denotes trifluoromethyl, methyl, ethyl, propyl, isopropyl, butyl or isobutyl, or denotes phenyl or naphthyl which are optionally monosubstituted or polysubstituted by methyl or chlorine, or denotes an —$NR^{10}R^{11}$ group, where
$R^{10}$ and $R^{11}$ have the abovementioned meaning,
$R^{16}$ denotes hydrogen, methyl, ethyl or propyl,
$R^{17}$ denotes hydrogen, or denotes methyl, ethyl, propyl, isopropyl, butyl or isobutyl, or denotes phenyl, and c denotes a number 2 to 4, and
$R^2$ and $R^3$ represent propyl,
and the salts thereof.

The following 8-substituted 2-aminotetralins may be mentioned as examples:
2-dipropylamino-8-chloro-1,2,3,4-tetrahydronaphthalene,
2-dipropylamino-8-bromo-1,2,3,4-tetrahydronaphthalene,
2-dipropylamino-8-cyano-1,2,3,4-tetrahydronaphthalene,
2-dipropylamino-8-(3-butyl-ureido)-1,2,3,4-tetrahydronaphthalene,
2-dipropylamino-8-formamido-1,2,3,4-tetrahydronaphthalene,
2-dipropylamino-8-carbamoyl-1,2,3,4-tetrahydronaphthalene,
2-dipropylamino-1,2,3,4-tetrahydronaphthalene-8-carboxylic acid,
2-dipropylamino-8-ethoxycarbonyl-1,2,3,4-tetrahydronaphthalene,
2-dipropylamino-8-formyl-1,2,3,4-tetrahydronaphthalene,
2-dipropylamino-8-hydroxymethyl-1,2,3,4-tetrahydronaphthalene,
2-dipropylamino-8-aminomethyl-1,2,3,4-tetrahydronaphthalene,
2-dipropylamino-8-aminomethyl-1,2,3,4-tetrahydronaphthalene hydrochloride,
2-dipropylamino-8-sulphonamidomethyl-1,2,3,4-tetrahydronaphthalene,
2-dipropylamino-8-butylsulphonamidomethyl-1,2,3,4-tetrahydronaphthalene,
2-dipropylamino-8-ethoxycarbonylamidomethyl-1,2,3,4-tetrahydronaphthalene,
2-dipropylamino-8-ethoxycarbonylamidomethyl-1,2,3,4-tetrahydroxynaphthalene hydrochloride,
2-dipropylamino-8-(3,3-diethylureido)methyl-1,2,3,4-tetrahydronaphthalene,
2-dipropylamino-8-ureidomethyl-1,2,3,4-tetrahydronaphthalene,
2-dipropylamino-8-(3-methylureido)methyl-1,2,3,4-tetrahydronaphthalene,
2-dipropylamino-8-formamidoethyl-1,2,3,4-tetrahydronaphthalene,
2-dipropylamino-8-(2-hydroxyethoxy)-1,2,3,4-tetrahydronaphthalene hydrochloride,
2-dipropylamino-8-carbamoylethoxy-1,2,3,4-tetrahydronaphthalene,
2-dipropylamino-8-(2-aminoethoxy)-1,2,3,4-tetrahydronaphthalene,
2-dipropylamino-8-(2-methanesulphonamido-methoxy)-1,2,3,4-tetrahydronaphthalene,
2-dipropylamino-8-(2-butylsulphonamido-ethoxy)-1,2,3,4-tetrahydronaphthalene,
2-dipropylamino-8-(2-propionylamido-ethoxy)-1,2,3,4,-tetrahydronaphthalene,
2-dipropylamino-8-(2-ethoxycarbonylamido-ethoxy)-1,2,3,4-tetrahydronaphthalene,
2-dipropylamino-8-[2-(3,3-diethylureido)ethoxy]-1,2,3,4-tetrahydronaphthalene,
2-dipropylamino-8-ureidoethoxy-1,2,3,4-tetrahydronaphthalene,
2-dipropylamino-8-[2-(3-methylureido)ethoxy]-1,2,3,4-tetrahydronaphthalene,
2-dipropylamino-8-[2-(3-butylureido)ethoxy]-1,2,3,4-tetrahydronaphthalene,
2-dipropylamino-8-(2-formylamido-ethoxy)-1,2,3,4-tetrahydronaphthalene,
2-dipropylamino-8-[2-(N,N-diethylaminosulphonyl)ethenyl]-1,2,3,4-tetrahydronaphthalene,
2-dipropylamino-8-[2-(N,N-dimethylaminosulphonyl)ethyl]-1,2,3,4-tetrahydronaphthalene,
2-dipropylamino-8-(2-nitro-ethenyl)-1,2,3,4-tetrahydronaphthalene,
2-dipropylamino-8-(2-amino-ethyl)-1,2,3,4-tetrahydronaphthalene,
2-dipropylamino-8-(2-methanesulphonamido-ethyl)-1,2,3,4-tetrahydronaphthalene hydrochloride,
2-dipropylamino-8-(2-butanesulphonamido-ethyl)-1,2,3,4-tetrahydronaphthalene,
2-dipropylamino-8-[2-(p-chlorobenzenesulphonamido)ethyl]-1,2,3,4-tetrahydronaphthalene,
2-dipropylamino-8-(2-ethoxycarbonylamido-ethyl)-1,2,3,4-tetrahydronaphthalene,
2-dipropylamino-8-(2-benzyloxycarbonylamido-ethyl)-1,2,3,4-tetrahydronaphthalene,
2-dipropylamino-8-(2-ureido-ethyl)-1,2,3,4-tetrahydronaphthalene,
2-dipropylamino-8-[2-(3-methylureido)ethyl]-1,2,3,4-tetrahydronaphthalene,
2-dipropylamino-8-(2-formylamido-ethyl)-1,2,3,4-tetrahydronaphthalene.

In the context of the present invention, the 8-halogeno-aminotetralins (Ia) correspond to the general formula

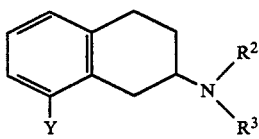
(Ia)

in which
$R^2$ and $R^3$ have the specified meaning and
Y represents halogen or cyano.

In the context of the present invention, the diaminotetralins (Ib) correspond to the general formula

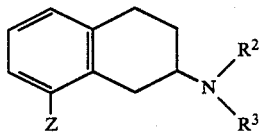
(Ib)

in which
Z represents a group of the formula $-NR^4R^5$, wherein
$R^4$ and $R^5$ are identical or different and denote hydrogen or a group of the formula $-COR^{7'}$ or $-SO_2R^8$, where
$R^{7'}$ represents hydrogen, or represents alkoxy, or represents aryl, aryloxy, aralkoxy, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, and
$R^8$ has the specified meaning and
$R^2$ and $R^3$ have the specified meaning.

In the context of the present invention, the 8-ureidoaminotetralins (Ic) correspond to the general formula

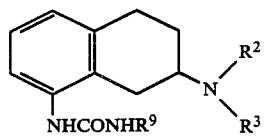
(Ic)

in which $R^2$, $R^3$ and $R^9$ have the specified meaning.

In the context of the present invention, the 8-acylaminotetralins (Id) correspond to the general formula

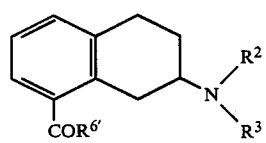
(Id)

in which
$R^{6'}$ represents hydroxyl, amino, alkoxy, aryloxy or aralkoxy, and
$R^2$ and $R^3$ have the specified meaning.

In the context of the present invention, the 8-formylaminotetralins (Ie) correspond to the general formula
(Ie)

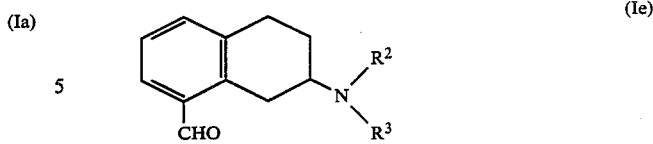
(Ie)

in which $R^2$ and $R^3$ have the specified meaning.

In the context of the present invention, the 8-methylene-aminotetralins (If) correspond to the general formula (If)

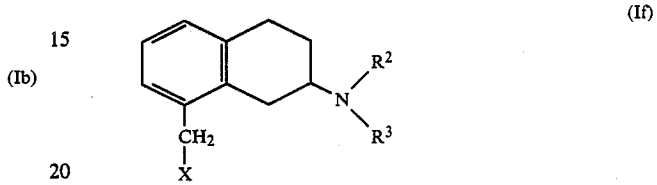
(If)

in which $R^2$, $R^3$ and X have the abovementioned meaning.

In the context of the present invention, the 8-alkylene-aminotetralins (Ig) correspond to the general formula

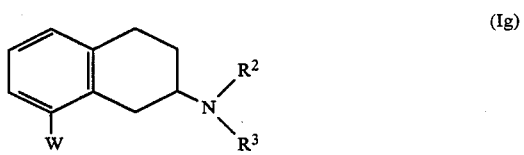
(Ig)

in which
W represents a group of the formula $-(CH_2)_{a'}-X$ or $-CH=CH-(CH_2)_b-X$,
$R^2$, $R^3$, X and b have the abovementioned meaning, and
$a'$ denotes a number 2 to 10.

In the context of the present invention, the 8-ethylene-aminotetralins (Ih) correspond to the general formula

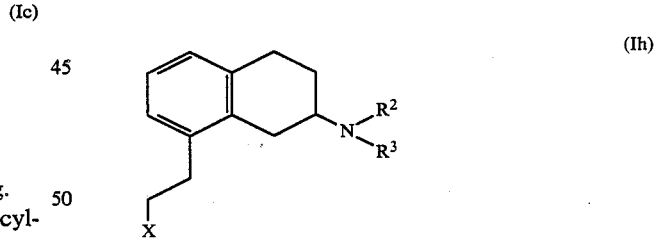
(Ih)

in which $R^2$, $R^3$ and X have the specified meaning.

A process has been found for the preparation of the 8-halogeno-aminotetralins, according to the invention, of the general formula (Ia)

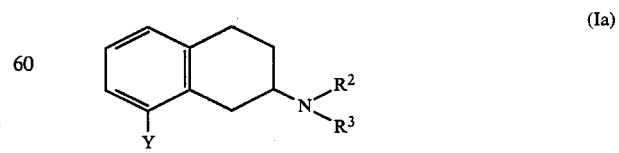
(Ia)

in which
Y represents halogen or cyano,
$R^2$ represents hydrogen or alkyl, and
$R^3$ represents alkyl, and the salts thereof, which is characterized in that

[A] 8-aminotetralins of the general formula (II)

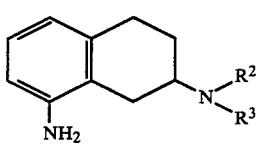
(II)

in which $R^2$ and $R^3$ have the specified meaning, are reacted with nitrites in inert solvents in the presence of acids, the diazonium salts obtained are then reacted with copper salts of the general formula (III)

CuY     (III)

in which Y has the specified meaning, if appropriate in the presence of auxiliaries, and, in the case of the preparation of the salts, are reacted with the appropriate acids, or in that

[B] tetralones of the general formula (IV)

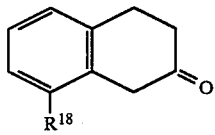
(IV)

in which $R^{18}$ represents chlorine or bromine, are initially reacted with amines of the general formula (V)

(V)

in which $R^2$ and $R^3$ have the specified meaning, in inert solvents, if appropriate in the presence of auxiliaries, then the intermediates are reduced in inert solvents, then, if appropriate, halogen is exchanged for cyano, and then, in the case of the preparation of the salts, the products are reacted with the appropriate acids.

The process according to the invention may be illustrated by the following equation:

Process version A:

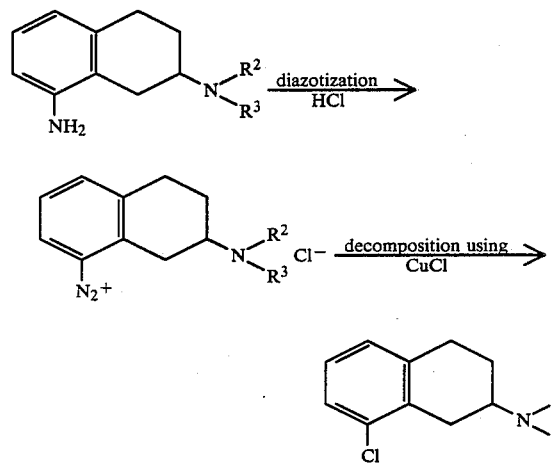

Process version B:

-continued

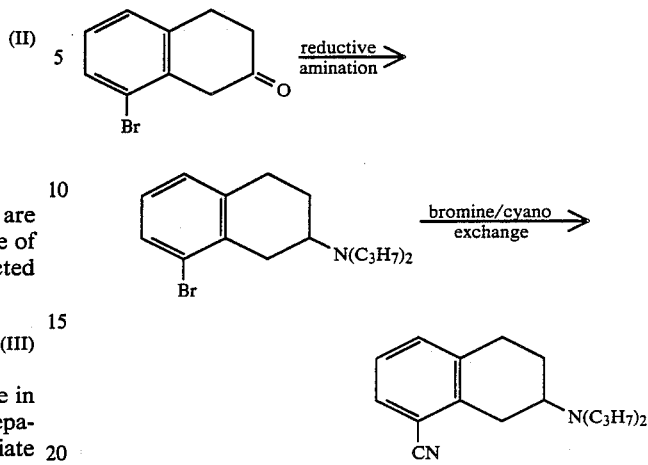

Process version A:

When carrying out process A according to the invention, the diazonium salts are generally produced as intermediates which can be isolated. However, it has proven expedient to carry out the process without isolating the intermediates.

Suitable inert solvents here are water or alcohols, such as methanol, ethanol, propanol or isopropanol, or amides, such as formamide or dimethylformamide, or acids, such as mineral acids or carboxylic acids. Water and/or acids, such as hydrochloric acid, hydrobromic acid, sulphuric acid, phosphoric acid or acetic acid, are preferred. It is likewise possible to employ mixtures of the solvents mentioned.

In general, mineral acids are employed as acids. Hydrochloric acid, hydrobromic acid, sulphuric acid or phosphoric acid, or mixtures of the acids mentioned, are preferred here.

In general, alkali metal nitrites, such as sodium or potassium nitrite, are used as nitrites. Sodium nitrite is preferably used.

In general, alkali metal or alkaline earth metal halides or cyanides are employed as auxiliaries. Sodium chloride, sodium bromide or sodium cyanide are preferred.

The reaction is generally carried out in a temperature range from $-10°$ C. to $+150°$ C., preferably from $0°$ C. to $100°$ C.

The reaction is generally carried out at atmospheric pressure. It is likewise possible to carry out the reaction at increased or reduced pressure (for example from 0.5 to 5 bar).

The process according to the invention is generally carried out in a fashion such that a solution of nitrite in water is initially added to the 8-aminotetralin in concentrated aqueous acids, and the reaction solution is subsequently treated with copper(I) halides or copper(I) cyanide, if appropriate dissolved in water. In general, the diazonium salt is not isolated. Hydrochloric acid and copper(I) chloride are preferably used for the introduction of the chlorine atom (Y=Cl), hydrobromic acid and copper(I) bromide for the introduction of the bromine atom (Y=Br), and sulphuric acid and copper(I) cyanide for the introduction of the nitrile function (Y=CN), if appropriate in the presence of sodium cyanide.

In general, work-up is effected by neutralization of the reaction mixture using alkali metal hydroxides or carbonates, and also extraction, crystallization and/or chromatography of the free bases thus obtained, from which the salts thereof are obtained by reaction with the appropriate acids.

The 8-aminotetralins employed as starting compounds are known [EP-A1 41,488].

The following 8-aminotetralins may be mentioned as examples:

8-amino-2-dimethylamino-1,2,3,4-tetrahydronaphthalene,
8-amino-2-diethylamino-1,2,3,4-tetrahydronaphthalene,
8-amino-2-dipropylamino-1,2,3,4-tetrahydronaphthalene,
8-amino-2-(N-ethyl-N-methyl)amino-1,2,3,4-tetrahydronaphthalene,
8-amino-2-(N-methyl-N-propyl)amino-1,2,3,4-tetrahydronaphthalene,
8-amino-2-(N-ethyl-N-propyl)amino-1,2,3,4-tetrahydronaphthalene.

Process version B:

The intermediates are prepared by reacting the tetralones (IV) with amines (V) in inert organic solvents, if appropriate in the presence of a catalyst and if appropriate in the presence of a dehydrating agent.

In the case of the reaction with primary amines, the intermediates are Schiff bases, and in the case of the reaction with secondary amines, the intermediates are enamines or immonium salts.

The process according to the invention may be carried out in two steps, that is to say with isolation of the intermediates. It is likewise possible to carry out the process according to the invention as a one-pot process.

Suitable inert solvents here are those conventional organic solvents which do not change under the reaction conditions. These preferably include alcohols such as methanol, ethanol, propanol or isopropanol, or ethers such as diethyl ether, butyl methyl ether, dioxane, tetrahydrofuran, glycol dimethyl ether or diethylene glycol dimethyl ether, or halogenated hydrocarbons such as, for example, methylene chloride, chloroform or carbon tetrachloride, or hydrocarbons such as benzene, toluene, xylene or petroleum fractions, or amides such as dimethylformamide or hexamethylphosphoric triamide, or acetic acid.

In addition, it is possible to use mixtures of the solvents mentioned.

In general, protonic acids are used as catalysts. These preferably include inorganic acids such as, for example, hydrochloric acid or sulphuric acid, or organic carboxylic acids having 1 to 6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

The water formed during the reaction may be removed, if appropriate, during or after the reaction as a mixture with the solvent used, for example by distillation or by addition of dehydrating agents, such as, for example, phosphorus pentoxide, or preferably by molecular sieve.

In general, the reaction is carried out in a temperature range from 0° C. to +200° C., preferably from +20° C. to +150° C.

In the case of removal of the water formed during the reaction by azeotropic distillation with the solvents used, the reaction is preferably carried out at the boiling temperature of the azeotrope.

The reaction can be carried out at atmospheric, elevated or reduced pressure (for example 0.5–5 bar). In general, the reaction is carried out at atmospheric pressure.

When carrying out the reaction, the starting materials are generally employed in a tetralone (IV) to amine (V) molar ratio of 0.5:2 to 1:2. Molar amounts of the reactants are preferably used.

The enamines are reduced either by hydrogen in water or inert organic solvents such as alcohols, ethers or halogenated hydrocarbons, or mixtures thereof, using catalysts such as Raney nickel, palladium, palladium on animal charcoal, or platinum, or using hydrides in inert solvents, if appropriate in the presence of a catalyst.

The reaction is preferably carried out using hydrides, such as complex borohydrides or aluminum hydrides. Sodium borohydride, Lithium aluminum hydride or sodium cyanoborohydride are particularly preferably employed here.

Suitable solvents in this reaction are all those inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoric triamide, or dimethylformamide, or acetic acid. It is likewise possible to use mixtures of the solvents mentioned.

In general, protonic acids are used as catalysts in the reduction. These preferably include inorganic acids such as, for example, hydrochloric acid or sulphuric acid, or organic carboxylic acids having 1–6 C atoms, optionally substituted by fluorine, chlorine and/or bromine, such as, for example, acetic acid, trifluoroacetic acid, trichloroacetic acid or propionic acid, or sulphonic acids having $C_1$–$C_4$-alkyl radicals or having aryl radicals, such as, for example, methanesulphonic acid, ethanesulphonic acid, benzenesulphonic acid or toluenesulphonic acid.

When carrying out the process according to the invention, it has proven favorable to carry out the reaction of the tetralones (IV) with the amines (V) as a one-pot process in an inert solvent, preferably in ethyl acetate or in alcohols such as, for example, methanol, ethanol, propanol or isopropanol, or mixtures thereof, in the presence of inorganic or organic acids, such as, for example, hydrochloric acid or acetic acid, and in the presence of a reducing agent, preferably complex hydrides such as, for example, sodium borohydride or sodium cyanoborohydride, if appropriate in the presence of a dehydrating agent, preferably a molecular sieve.

In this case, the reaction is carried out in a temperature range from 0° C. to +150° C., preferably from 0° C. to +100° C., at atmospheric pressure. It is likewise possible to carry out the reaction at reduced pressure or at increased pressure (for example in a Carius tube).

If the process according to the invention is carried out as a one-pot reaction, it has proven favorable to employ the amine in an excess of up to 10-fold, preferably up to 5-fold, compared to the tetralone.

The substitution of cyano for halogen, particularly bromine, is generally carried out using copper(I) cyanide in inert solvents, preferably amides such as dimethylformamide or hexamethylphosphoric triamide, in a temperature range from +20° C. to +200° C., preferably from +50° C. to +150° C., at atmospheric pressure.

The amines employed as starting materials are known or can be prepared by known processes (Houben-Weyl's "Methoden der organischen Chemie" [Methods of Organic Chemistry] XI/1 and XI/2).

The following amines may be mentioned as examples: methylamine, ethylamine, propylamine, dimethylamine, diethylamine, dipropylamine, methyl-propylamine, ethylmethylamine and ethyl-propylamine.

Some of the tetralones employed as starting materials are new and can be prepared by methods, known per se, of Friedel-Crafts acylation from 2-halogeno-phenylacetyl chlorides or bromides, aluminum chloride and ethers (Houben-Weyl's "Methoden der organischen Chemie" [Methods of Organic Chemistry] VII/2a, 141; G. P. Johnson, Org. Synth., Coll. Vol. IV, 900 (1963)).

The following tetralones may be mentioned as examples:
8-chloro-2-tetralone and 8-bromo-2-tetralone.

In addition, a process has been found for the preparation of the diaminotetralins, according to the invention, of the general formula (Ib)

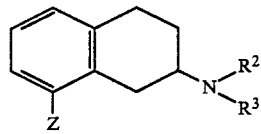

(Ib)

wherein
Z represents a group of the formula —NR$^4$R$^5$, wherein
R$^4$ and R$^5$ are identical or different and denote hydrogen, or a group of the formula —COR$^{7'}$ or —SO$_2$R$^8$, where
R$^{7'}$ represents hydrogen, or represents alkoxy, or represents aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, and
R$^8$ represents cycloalkyl, or represents alkyl which may be substituted by cyano, halogen, trifluoromethyl, trifluoromethoxy or alkoxycarbonyl, or represents aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or represents an —NR$^{10}$R$^{11}$ group, wherein
and R$^{11}$ are identical or different and denote hydrogen, alkyl, aryl or aralkyl,
R$^2$ represents hydrogen or alkyl, and
R$^3$ represents alkyl, but where
R$^1$ does not denote NH$_2$ when
R$^2$ and R$^3$ denote propyl and the salts thereof, which is characterized in that 8-aminotetralins of the general formula (II)

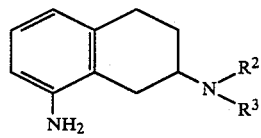

(II)

in which
R$^2$ and R$^3$ have the abovementioned meaning, are reacted with acylating or sulphonating agents of the general formula (VI)

 V—R$^{19}$ (VI)

in which
R$^{19}$ represents a group of the formula —COR$^7$ or —SO$_2$R$^8$, and
V represents halogen, or represents the —OR$^{20}$ radical, wherein
R$^{20}$ has the same meaning as R$^{19}$ and can be identical to or different from the latter,
in inert solvents, if appropriate in the presence of bases, and then, in the case of the preparation of the salts, the products are reacted with the appropriate acids.

The process according to the invention may be illustrated by the following equation:

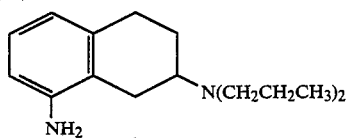

(a)

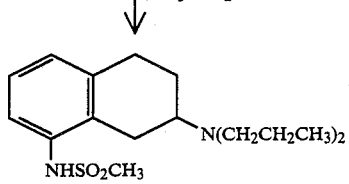

(b)

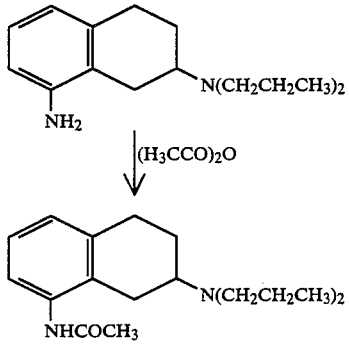

Suitable inert solvents here are those conventional organic solvents which do not change under the reaction conditions. These preferably include ethers such as diethyl ether, butyl methyl ether, dioxane, tetrahydrofuran, glycol dimethyl ether or diethylene glycol dimethyl ether, or halogenated hydrocarbons such as, for example, methylene chloride, chloroform, carbon tetrachloride, dichloroethane, dichloroethylene or trichloroethylene, or hydrocarbons such as benzene, toluene, xylene, or petroleum fractions, or alcohols such as methanol, ethanol, propanol or isopropanol, or carboxylic acids such as formic acid, acetic acid or propionic acid, or carboxylic acid anhydrides such as propionic anhydride or acetic anhydride, or acetone, ethyl acetate or acetonitrile. It is likewise possible to employ mixtures of the solvents mentioned.

The conventional basic compounds may be employed as bases for basic reactions. These preferably include alkali metal or alkaline earth metal hydroxides( or alkali metal or alkaline earth metal carbonates, such as, for example, lithium hydroxide, sodium hydroxide, potassium hydroxide or barium hydroxide, sodium carbonate, potassium carbonate or sodium bicarbonate, or alkali metal alcoholates such as, for example, sodium methanolate, sodium ethanolate, potassium methanolate or potassium ethanolate, or alkali metal amides such as sodium amide or lithium diisopropylamide, or organic amines such as triethylamine, tripropylamine, pyridine, piperidine or N,N-dimethylaminopyridine.

The reaction is generally carried out in a temperature range from $-30°$ C. to $+100°$ C., preferably from $0°$ C. to $+80°$ C.

The reaction is generally carried out at atmospheric pressure. It is likewise possible to carry out the reaction at increased or reduced pressure (for example from 0.5 to 5 bar).

In general, carboxylic acid halides or anhydrides, preferably carboxylic acid chlorides or bromides or symmetrical or asymmetrical carboxylic acid anhydrides, are used as acylating agents (general formula VI with $R^{19}=COR^7$), mixed anhydrides with formic acid, acetic acid or propionic acid preferably being used in the case of the asymmetrical anhydrides.

In general, sulphonyl halides or sulphonic anhydrides, preferably sulphonyl chlorides or bromides, or symmetrical or asymmetrical sulphonic anhydrides, are employed as sulphonating agents (general formula VI with $R^{19}=SO_2R^8$), mixed anhydrides with methanesulphonic, ethanesulphonic, benzenesulphonic or toluenesulphonic acid preferably being used in the case of asymmetrical anhydrides.

When carrying out the process according to the invention, the acylating or sulphonating agents are generally employed in an amount from 1 to 10 moles, preferably from 1 to 5 moles, relative to 1 mole of the 8-aminotetralin. The base is generally employed in an amount from 1 to 5, preferably from 1 to 2 moles, relative to 1 mole of the acylating or sulphonating agent.

In addition, a process has been found for the preparation of the 8-ureido-aminotetralins, according to the invention, of the general formula (Ic)

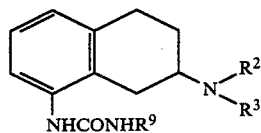

in which
R² represents hydrogen or alkyl,
R³ represents alkyl and
R⁹ represents hydrogen, or represents cycloalkyl, or represents alkyl which is optionally substituted by cyano, halogen, trifluoromethyl or trifluoromethoxy, or represents aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino,
and the salts thereof, which is characterized in that 8-aminotetralins of the general formula (II)

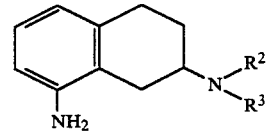

in which $R^2$ and $R^3$ have the specified meaning, are reacted with isocyanates of the general formula (VII)

$$R^9N=C=O \qquad (VII)$$

in which $R^9$ has the specified meaning, in inert solvents, if appropriate in the presence of bases, and then, in the case of the preparation of the salts, the products are reacted with the appropriate acids.

The process according to the invention may be illustrated by the following equation:

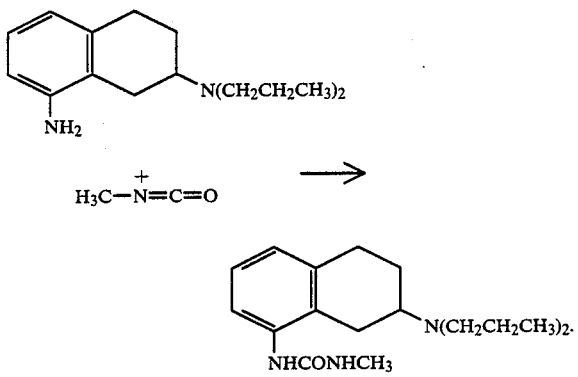

Suitable inert solvents are those conventional organic solvents which do not change under the reaction conditions. These preferably include ethers such as diethyl ether, butyl methyl ether, dioxane, tetrahydrofuran or glycol dimethyl ether, or halogenated hydrocarbons such as, for example, methylene chloride, chloroform, carbon tetrachloride, dichloroethane, dichloroethylene or trichloroethylene, or hydrocarbons such as benzene, toluene, xylene or petroleum fractions, or amides such as dimethylformamide or hexamethylphosphoric triamide, or acetic acid, acetonitrile or pyridine. It is likewise possible to employ mixtures of the solvents mentioned.

Suitable bases here are the conventional organic amines. These preferably include trialkylamines such as, for example, triethylamine or tripropylamine, or tertiary organic bases such as, for example, pyridine, N,N-dimethylaminopyridine, picoline, piperidine, morpholine or 1,5-diazabicyclo [4,3,0]non-5-ene or 1,5-diazabicyclo[5,4,0]undec-5-ene.

The reaction is generally carried out in a temperature range from $-30°$ C. to $+100°$ C., preferably from $0°$ C. to $+80°$ C.

The reaction is generally carried out at atmospheric pressure. It is likewise possible to carry out the reaction at increased or reduced pressure (for example from 0.5 to 5 bar).

When carrying out the process according to the invention, the isocyanates are generally employed in an amount from 1 to 3, preferably from 1 to 2 moles, relative to 1 mole of the 8-aminotetralin. The base is generally employed in an amount from 0.01 to 1 mole, preferably from 0.1 to 0.5 mole, relative to 1 mole of the isocyanate.

The process can be carried out, for example, by mixing the 8-aminotetralin with isocyanate and base in an inert solvent, and wa[r]ming, if appropriate. Work-up is effected by extraction, chromatography and/or crystallization.

In the case of the preparation of the unsubstituted 8-ureido-aminotetralins ($R^9$=H), alkali metal cyanates, preferably sodium or potassium cyanate, are employed in water and/or acids such as hydrochloric acid, hydrobromic acid or sulphuric acid.

In addition, a process has been found for the preparation of the 8-acyl-aminotetralins, according to the invention, of the-general formula (Id)

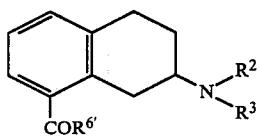
(Id)

in which
$R^2$ represents hydrogen or alkyl,
$R^3$ represents alkyl and
$R^{6'}$ represents hydroxyl, amino, alkoxy, aryloxy or aralkoxy, and the salts thereof,
which is characterized in that 8-cyanotetralins of the general formula (VIII)

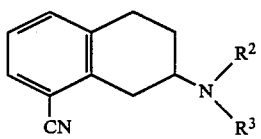
(VIII)

in which $R^2$ and $R^3$ have the abovementioned meaning, are hydrolyzed, and, in the case of the preparation of the carboxylates, the carboxylic acids obtained are esterified and, in the case of the preparation of the salts, reacted with the appropriate acids.

The process according to the invention may be illustrated by the following equation:

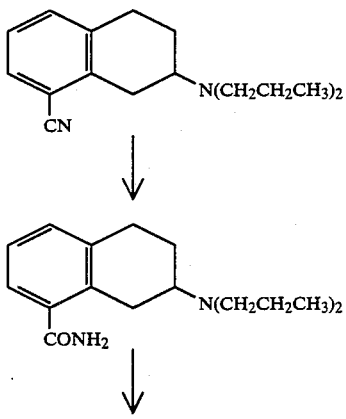

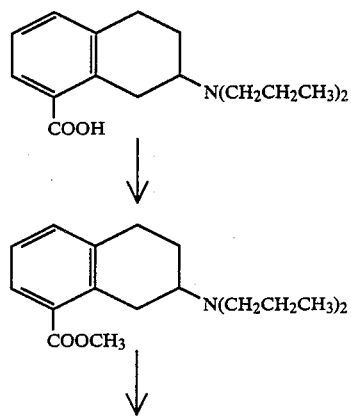

During the hydrolysis when carrying out the process according to the invention, the amides are generally produced first and then the carboxylic acids. The carboxylic acids can also be prepared without isolating the amides. The esters according to the invention are obtained by esterifying the carboxylic acids. This reaction can also be carried out without isolating the amides or the carboxylic acids. The carboxylic acids are preferably prepared in one step without isolating the amides, but, in contrast, the carboxylates are prepared from the isolated carboxylic acids.

The hydrolysis to form the amides or carboxylic acids according to the invention is generally carried out using water in inert solvents in the presence of bases.

Suitable inert solvents here are water or alcohols such as methanol, ethanol, propanol, isopropanol or butanol or glycol, or amides such as dimethylformamide or hexamethylphosphoric triamide, or ethers such as dioxane, tetrahydrofuran, glycol monomethyl ether, glycol dimethyl ether or diethyl glycol dimethyl ether. It is likewise possible to employ mixtures of the solvents mentioned.

Suitable bases for the hydrolysis are the conventional basic compounds. These preferably include alkali metal or alkaline earth metal hydroxides, such as sodium hydroxide, potassium hydroxide or barium hydroxide, or alkali metal carbonates such as, for example, sodium carbonate, sodium bicarbonate or potassium carbonate, or alkali metal alcoholates such as, for example, sodium methanolate, sodium ethanolate, potassium methanolate, potassium ethanolate or potassium tert.butanolate.

The hydrolysis is generally carried out in a temperature range from 0° C. to +200° C., preferably from +20° C. to +150° C.

The hydrolysis is generally carried out at atmospheric pressure. It is likewise possible to carry out the reaction at increased or at reduced pressure (for example from 0.5 to 5 bar).

When carrying out the hydrolysis according to the invention, the bases are generally employed in an amount from 1 to 10, preferably from 1 to 5 moles, relative to 1 mole of the 8-cyano-aminotetralins.

The esterification of the carboxylic acids according to the invention to form the carboxylates according to the invention is generally carried out using the appropriate alcohols in the presence of acids in inert solvents.

Suitable inert solvents here are those conventional organic solvents which do not change under the reaction conditions. These preferably include alcohols such as methanol, ethanol, propanol, isopropanol or butanol, or ethers such as diethyl ether, dioxane or tetrahydrofuran, or halogenated hydrocarbons such as methylene chloride, chloroform or carbon tetrachloride. It is likewise possible to employ mixtures of the solvents mentioned.

Suitable acids for the esterification are the conventional inorganic acids. These preferably include mineral acids such as hydrochloric acid, hydrobromic acid, sulphuric acid or phosphoric acid.

The esterification is generally carried out in a temperature range from +10° C. to +150° C., preferably from 20° C. to +100° C.

The esterification is generally carried out at atmospheric pressure. It is likewise possible to carry out the esterification at increased or reduced pressure (for example at 0.5 to 5 bar).

When carrying out the esterification, the acids are generally employed in an amount from 1 to 50, preferably from 1 to 20 moles, relative to 1 mole of the carboxylic acid. The alcohols are generally employed in excess. It has proven favorable here to simultaneously employ the alcohols with which the esterification is carried out as solvents.

An ethereal or alcoholic hydrogen chloride solution is preferably used as acid, the alcohol with which the carboxylic acid is esterified itself being used as alcohol.

The process according to the invention may be carried out, for example, in the following fashion: the 8-cyano-aminotetralin is Warmed in an inert solvent together with a base, the length of the reaction and the temperature level being dependent on whether the carboxylic acid amide or the carboxylic acid is to be prepared. For the esterification, the appropriate carboxylic acid is warmed in an inert solvent in the presence of an acid, during which the resultant water of reaction can be removed, together with the solvent, by distillation, if appropriate.

The 8-cyano-aminotetralins employed as starting materials are new and can be prepared by the process described above.

The following may be used, for example, according to the invention as 8-cyano-aminotetralins:

8-cyano-2-dimethylamino-1,2,3,4-tetrahydronaphthalene,
8-cyano-2-diethylamino-1,2,3,4-tetrahydronaphthalene,
8-cyano-2-dipropylamino-1,2,3,4-tetrahydronaphthalene,
8-cyano-2-(N-ethyl-N-methyl)amino-1,2,3,4-tetrahydronaphthalene,
8-cyano-2-(N-ethyl-N-propyl)amino-1,2,3,4-tetrahydronaphthalene,
8-cyano-2-(N-methyl-N-propyl)amino-1,2,3,4-tetrahydronaphthalene.

In addition, a process has been found for the preparation of the 8-formyl-aminotetralins, according to the invention, of the general formula (Ie)

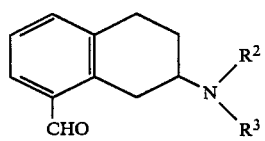

(Ie)

in which
$R^2$ represents hydrogen or alkyl, and
$R^3$ represents alkyl, and the salts thereof, which is characterized in that 8-halogen-substituted 2-aminotetralins of the general formula (IX)

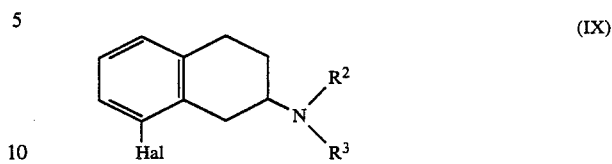

(IX)

in which
$R^2$ and $R^3$ have the abovementioned meaning and
Hal represents fluorine, chlorine, bromine, iodine, preferably chlorine or bromine,
are reacted with magnesium and formamides of the general formula (X)

(X)

in which
$R^{21}$ and $R^{22}$ are identical or different and represent methyl, ethyl, propyl, phenyl or pyridyl, or
$R^{21}$ and $R^{22}$, together with the nitrogen atom, form a piperidine ring,
in inert solvents, if appropriate in the presence of auxiliaries, and then, in the case of the preparation of the salts, the products are reacted with the appropriate acids.

The process according to the invention may be illustrated by the following equation:

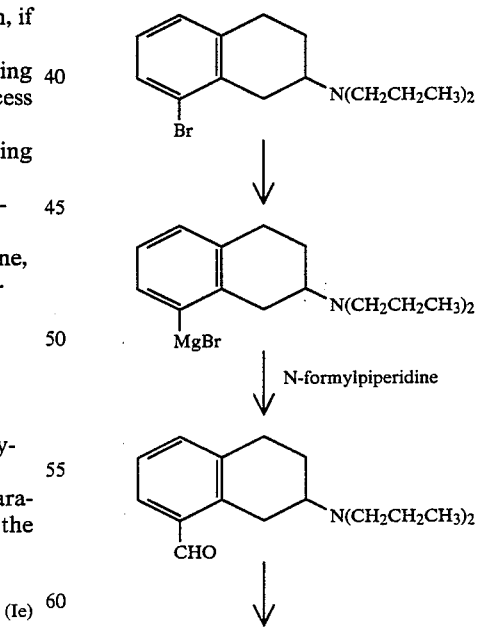

Suitable inert solvents here are those conventional organic solvents which do not change under the reaction conditions. These preferably include ethers such as diethyl ether, butyl methyl ether, dioxane or tetrahydrofuran, or hydrocarbons such as benzene, toluene or xylene, or amides such as dimethylformamide or hexamethylphosphoric triamide. It is likewise possible to employ mixtures of the solvents mentioned.

In general, substances are employed as auxiliaries as are conventional for the activation of a Grignard reaction. These preferably include iodine or organoiodine compounds, or anthracene, preferably iodine or iodoethane.

The reaction is generally carried out in a temperature range from −30° C. to +100° C., preferably from 0° C. to +50° C.

The reaction is generally carried out at atmospheric pressure. It is likewise possible to carry out the reaction at increased or reduced pressure (for example from 0.5 to 5 bar).

When carrying out the process according to the invention, the formamides are generally employed in an amount from 1 to 5 moles, preferably from 1 to 2 moles, relative to 1 mole of the starting compound.

The process according to the invention may be carried out, for example, in the following fashion: magnesium powder or magnesium turnings are initially introduced into a suitable solvent, a solution of the 8-halogensubstituted 2-aminotetralin in a suitable solvent is added dropwise, and the appropriate formamide, if appropriate dissolved in an inert solvent, is subsequently added to the reaction mixture. After hydrolysis of the reaction mixture, work-up is effected by extraction, chromatography and/or crystallization.

The 8-halogen-substituted 2-aminotetralins employed as starting materials are new and can be prepared by the process already described above.

The following may be used, for example, according to the invention as 8-halogen-substituted 2-aminotetralins:

8-bromo-2-dimethylamino-1,2,3,4-tetrahydronaphthalene,
8-bromo-2-diethylamino-1,2,3,4-tetrahydronaphthalene,
8-bromo-2-dipropylamino-1,2,3,4-tetrahydronaphthalene,
8-chloro-2-dimethylamino-1,2,3,4-tetrahydronaphthalene,
8-chloro-2-diethylamino-1,2,3,4-tetrahydronaphthalene,
8-chloro-2-dipropylamino-1,2,3,4-tetrahydronaphthalene,
8-bromo-2-(N-ethyl-N-methyl)amino-1,2,3,4-tetrahydronaphthalene,
8-bromo-2-(N-ethyl-N-propyl)amino-1,2,3,4-tetrahydronaphthalene,
8-bromo-2-(N-methyl-N-propyl)amino-1,2,3,4-tetrahydronaphthalene,
8-chloro-2-(N-ethyl-N-methyl)amino-1,2,3,4-tetrahydronaphthalene,
8-chloro-2-(N-ethyl-N-propyl)amino-1,2,3,4-tetrahydronaphthalene,
8-chloro-2-(N-methyl-propyl)amino-1,2,3,4-tetrahydronaphthalene.

In addition, a process has been found for the preparation of the 8-methylene-aminotetralins, according to the invention, of the general formula (If)

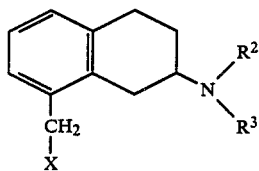

in which
$R^2$ represents hydrogen or alkyl,
$R^3$ represents alkyl and
X denotes a group of the formula $-NR^{12}R^{13}$, $-COR^{14}$, $-SO_2R^{15}$ or $-OR^{16}$, wherein
$R^{12}$ and $R^{13}$ are identical or different and represent hydrogen, alkyl, aryl or aralkyl, where the aryl radicals may be substituted by halogen, cyano, alkyl, alkoxy or trifluoromethyl, or represent a group of the formula $-COR^{14}$, $-SO_2R^{15}$ or $-(CH_2)_c-NR^{12}R^{13}$,
$R^{14}$ denotes hydrogen, or denotes an $-NHR^{17}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino,
$R^{15}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or denotes an $-NR^{10}R^{11}$ group, where
$R^{10}$ and $R^{11}$ are identical or different and represent hydrogen, alkyl, aryl or aralkyl,
$R^{16}$ denotes hydrogen, alkyl, aryl, aralkyl or a group of the formula $-COR^{10}R^{11}$,
$R^{17}$ denotes hydrogen, or denotes cycloalkyl, or denotes alkyl which is optionally substituted by cyano, halogen, trifluoromethyl or trifluoromethoxy, or denotes aryl, aralkyl or heteroaryl, where the aryl radical may be up to trisubstituted, identically or differently, by alkyl, alkoxy, alkylthio, halogen, cyano, trifluoromethyl, trifluoromethoxy, trifluoromethylthio, amino, alkylamino or dialkylamino, and
c denotes a number 1 to 8, or where
$R^{12}$ and $R^{13}$, together with the nitrogen atom, form a ring from the series comprising

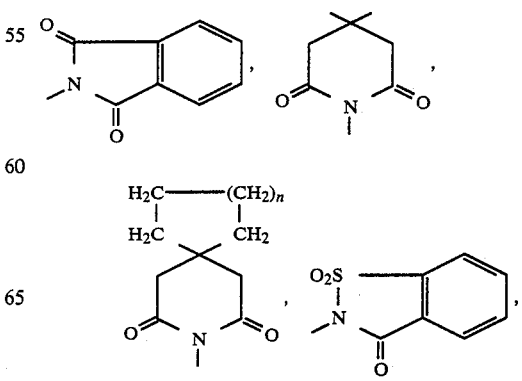

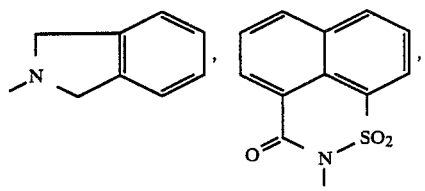

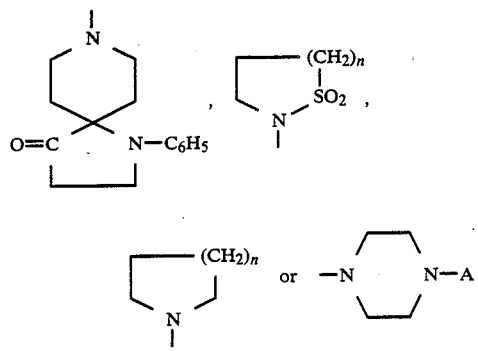

wherein
n denotes a number 1 or 2, and
A represents hydrogen or cycloalkyl, or represents alkyl which may be substituted by halogen, hydroxyl, amino, alkylamino, dialkylamino, carbamoyl or sulphamoyl, or represents aryl, heteroaryl, aralkyl, alkoxycarbonyl, alkylsulphonyl, phenylsulphonyl, tolylsulphonyl, benzylsulphonyl, formyl, carbamoyl or sulphamoyl,
$R^2$ represents hydrogen or alkyl, and
$R^3$ represents alkyl, but where
$R^1$ does not denotes $NH_2$ when
$R^2$ and $R^3$ denote propyl, and the salts thereof,
which is characterized in that tetralins of the general formula (XI)

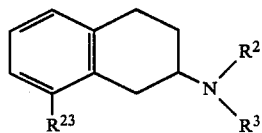

(XI)

in which
$R^2$ represents hydrogen or alkyl,
$R^3$ represents alkyl, and
$R^{23}$ represents a group of the formula $-COR^{24}$ or $-CN$, wherein
$R^{24}$ denotes hydrogen, hydroxyl, alkoxy or amino,
are reduced in inert solvents, then, if appropriate, functional groups are converted into other functional groups by reduction, hydrolysis, oxidation or reaction with electrophilic reagents, and then, in the case of the preparation of the salts, the products are reacted with the appropriate acid.

The process according to the invention may be illustrated, for example, by the following equation:

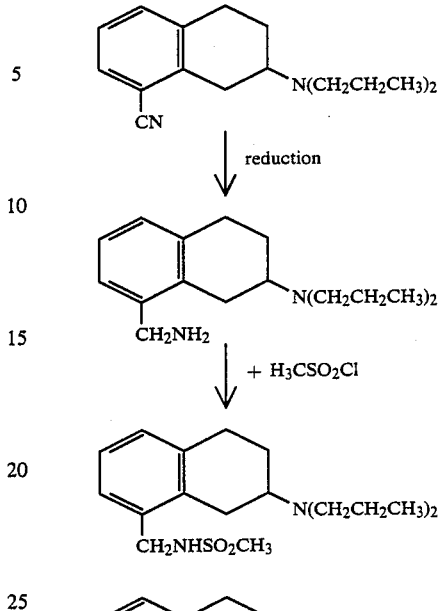

(a)

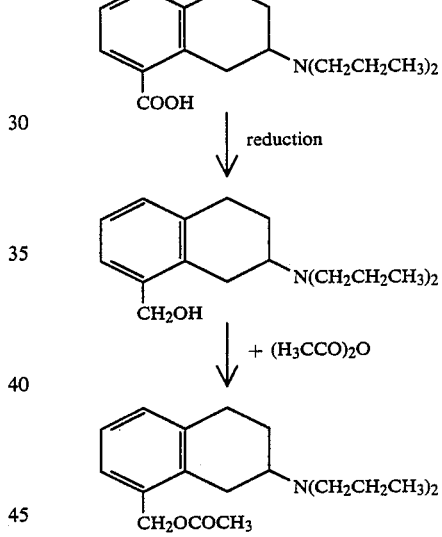

(b)

The reduction is carried out either by means of hydrogen in water or inert organic solvents such as alcohols, ethers or halogenated hydrocarbons, or mixtures thereof, using catalysts such as metals or noble metals or salts thereof, such as, for example, Raney nickel, palladium, palladium on animal charcoal, platinum or platinum oxide, or using hydrides in inert solvents, if appropriate in the presence of a catalyst.

The reduction is preferably carried out using metal hydrides or complex metal hydrides, such as aluminium hydrides or complex borohydrides or aluminum hydrides. Sodium borohydride, lithium aluminum hydride, sodium aluminum hydride, aluminum hydride, sodium cyanoborohydride or lithium trimethoxy-hydridoaluminate, if appropriate in the presence of aluminum chloride, are particularly preferably employed here.

Suitable solvents are all those inert organic solvents which do not change under the reaction conditions. These preferably include alcohols such as methanol, ethanol, propanol or isopropanol, or ethers such as diethyl ether, dioxane, tetrahydrofuran, glycol dimethyl ether or diethylene glycol dimethyl ether, or amides such as hexamethylphosphoric triamide or dimethylformamide, or acetic acid, trichloroacetic acid or trifluoroacetic acid, or halogenated hydrocarbons such as methylene chloride, chloroform or carbon tetrachloride. It is likewise possible to use mixtures of the solvents mentioned.

In general, acids are used as catalysts in the reduction. These preferably include inorganic acids such as hydrochloric acid, hydrobromic acid or sulphuric acid, or organic carboxylic acids having 1 to 4 carbon atoms, or sulphonic acids having 1 to 4 carbon atoms, such as, for example, formic acid, acetic acid, propionic acid, trichloroacetic acid, trifluoroacetic acid, methanesulphonic acid, ethanesulphonic acid, benzenesulphonic acid or toluenesulphonic acid.

The reduction is particularly preferably carried out in inert solvents, preferably in ethyl acetate or in alcohols such as, for example, methanol, ethanol, propanol or isopropanol, or mixtures thereof, in the presence of inorganic or organic acids, such as, for example, hydrochloric acid or acetic acid, and in the presence of a reducing agent, preferably complex hydrides such as, for example, sodium borohydride, lithium aluminum hydride or sodium cyanoborohydride.

The reduction is generally carried out in a temperature range from $-20°$ C. to $+100°$ C., preferably from $0°$ C. to $+80°$ C.

The reduction is generally carried out at atmospheric pressure. It is likewise possible to carry out the reaction at reduced or increased pressure (for example from 0.5 to 5 bar).

When carrying out the reduction, the reducing agent is generally employed in an amount from 1 to 6, preferably from 1 to 3 moles, relative to 1 mole of the starting compound.

The process according to the invention can be carried out, for example, by adding the tetralins, if appropriate in an inert solvent, to the reducing agent in an inert solvent, and, if appropriate, warming. Work-up is effected in a conventional fashion by extraction, chromatography and/or crystallization.

In addition, a process has been found for the preparation of the 8-alkylene-aminotetralins, according to the invention, of the general formula (Ig)

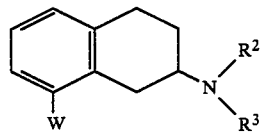

(Ig)

in which
$R^2$ represents hydrogen or alkyl,
$R^3$ represents alkyl, and
W represents a group of the formula $-(CH_2)_{a'}-X$ or $-CH=CH-(CH_2)_b-X$, wherein X denotes a group of the formula $-NR^{12}R^{13}$, $-COR^{14}$, $-SO_2R^{15}$ or $-OR^{16}$, wherein
$R^{12}$ and $R^{13}$ are identical or different and represent hydrogen, alkyl, aryl or aralkyl, where the aryl radicals may be substituted by halogen, cyano, alkyl, alkoxy or trifluoromethyl, or represent a group of the formula $-COR^{14}$, $-SO_2R^{15}$ or $-(CH_2)_c-NR^{12}R^{13}$,
$R^{14}$ denotes hydrogen, or denotes an $-NHR^{17}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino,
$R^{15}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or denotes an $-NR^{10}R^{11}$ group, where
$R^{10}$ and $R^{11}$ have the abovementioned meaning,
$R^{16}$ denotes hydrogen, alkyl, aryl, aralkyl or a group of the formula $-CONR^{10}R^{11}$,
$R^{17}$ denotes hydrogen, or denotes cycloalkyl, or denotes alkyl which is optionally substituted by cyano, halogen, trifluoromethyl or trifluoromethoxy, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, and
c denotes a number 1 to 8, or where
$R^{12}$ and $R^{13}$, together with the nitrogen atom, form a ring from the series comprising

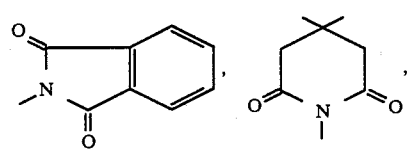

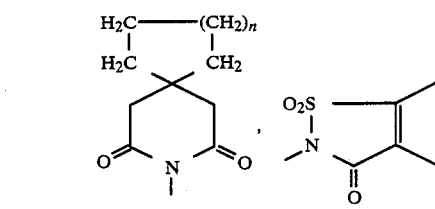

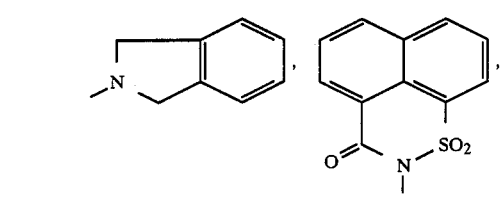

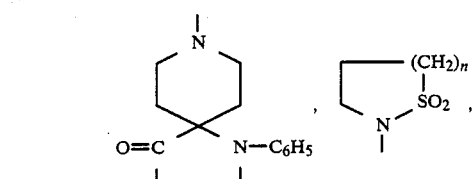

-continued

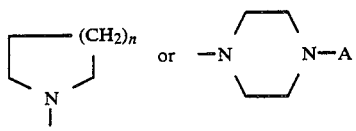

wherein
n denotes a number 1 or 2, and
A represents hydrogen or cycloalkyl, or represents alkyl which may be substituted by halogen, hydroxyl, amino, alkylamino, dialkylamino, carbamoyl or sulphamoyl, or represents aryl, heteroaryl, aralkyl, alkoxycarbonyl, alkylsulphonyl, phenylsulphonyl, tolylsulphonyl, benzylsulphonyl, formyl, carbamoyl or sulphamoyl, and
a' denotes a number 2 to 10 and
b denotes a number 0 to 8,
and the salts thereof, which is characterized in that 8-formyl-aminotetralins of the general formula (Ie)

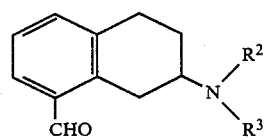

(Ie)

in which $R^2$ and $R^3$ have the specified meaning, are reacted with phosphorus compounds of the general formula (XII)

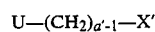 (XII)

in which
X' has the meaning given for X, or represents nitro,
a' has the abovementioned meaning and
U represents a group of the formula

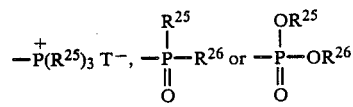

where
$R^{25}$ and $R^{26}$ are identical or different and denote alkyl or phenyl, and
T denotes a halide anion, preferably chloride, bromide or iodide,
in inert solvents in the presence of bases, then, if appropriate, functional groups are converted into other functional groups by reduction, hydrolysis, oxidation or reaction with electrophilic reagents, and then, in the case of the preparation of the salts, the products are reacted with the appropriate acids.

The process according to the invention may be illustrated by the following equation:

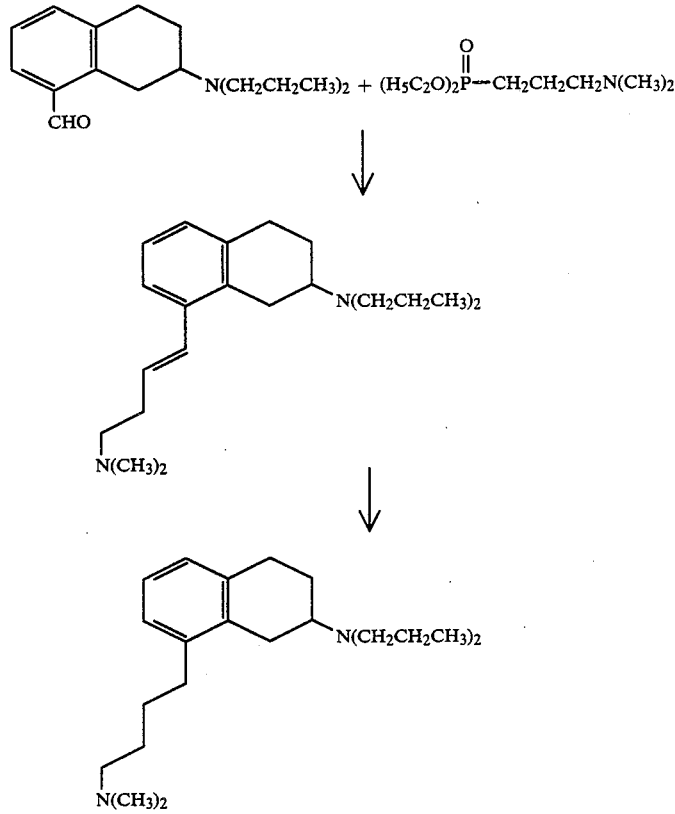

Suitable inert solvents here are those conventional organic solvents which do not change under the reaction conditions. These preferably include ethers such as diethyl ether, butyl methyl ether, dioxane, tetrahydrofuran, glycol dimethyl ether or diethylene glycol dimethyl ether, or hydrocarbons such as benzene, toluene, xylene or petroleum fractions, or amides such as dimethylformamide or hexamethylphosphoric triamide, or alcohols such as methanol, ethanol, propanol or isopropanol, or dimethyl sulphoxide. It is likewise possible to use mixtures of the solvents mentioned.

Suitable bases are the conventional basic compounds for basic reactions. These preferably include alkali metal or alkaline earth metal hydroxides, such as, for example, sodium hydroxide, potassium hydroxide or barium hydroxide, or alkali metal carbonates such as sodium carbonate, sodium bicarbonate or potassium carbonate, or alkali metal alcoholates such as sodium methanolate, sodium ethanolate, potassium methanolate, potassium ethanolate or potassium tert.butylate, or amides such as sodium amide or lithium diisopropylamide, or organolithium compounds such as phenyllithium or butyllithium.

The choice of solvent or base depends on the stability, sensitivity to hydrolysis or CH acidity of the appropriate phosphorus compound. Ethers such as diethyl ether, tetrahydrofuran or dioxane, or hydrocarbons such as benzene, toluene or xylene, or dimethylformamide are particularly preferably used as solvent. Alkali metal alcoholates such as sodium methanolate, sodium ethanolate, potassium methanolate, potassium ethanolate or potassium tert.butylate, or organolithium compounds such as phenyllithium or butyllithium are particularly preferably used as bases.

The reaction is generally carried out in the temperature range from $-30°$ C. to $+150°$ C., preferably from $0°$ C. to $+100°$ C.

The reaction may be carried out at atmospheric, increased or at reduced pressure (for example 0.5 to 5 bar). In general, the reaction is carried out at atmospheric pressure.

When carrying out the reaction, the phosphorus compounds are generally employed in an amount from 1 to 2 moles, preferably in molar amounts, relative to 1 mole of the 8-formyl-aminotetralins. The bases are generally employed in an amount from 1 to 5, preferably from 1 to 2 moles, relative to 1 mole of the phosphorus compound.

The process according to the invention can be carried out, for example, by adding the base and then the 8-formyl-aminotetralins, if appropriate in a suitable solvent, to the phosphorus compounds, dissolved or suspended in a suitable solvent, and, if appropriate, warming. The work-up is effected in a conventional fashion by extraction, chromatography and/or crystallization.

When carrying out the process according to the invention, it is likewise possible to employ the appropriate phosphoranes $[(R^{25})_3P=CH-(CH_2)_{a'-2}-X]$, which have previously been prepared from the appropriate phosphonium salts and bases in a separate reaction, directly in place of the phosphonium salts $(U=-P(R^{25})_3+T^-)$. However, it has proven favorable to carry out the reaction with the phosphorus compounds in the presence of bases as a one-pot process. As a particular variant of a one-pot process, the reaction may also be carried out, depending on the stability of the phosphorus compounds, in the form of a phase transfer-catalyzed reaction, where ether, hydrocarbons and halogenated hydrocarbons may be used as solvents and aqueous sodium hydroxide or potassium hydroxide solutions may be employed as bases.

The phosphorus compounds of the general formula (XII) employed as starting materials are known or can be prepared by known methods (Houben-Weyl's "Methoden der organischen Chemie" [Methods of Organic Chemistry] Vol. XII/1, 33, 167).

In addition, a process version has been found for the preparation of the 8-ethylene-aminotetralins, according to the invention, of the general formula (Ih)

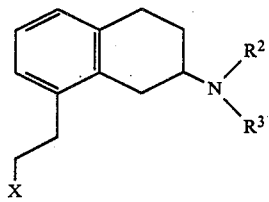

(Ih)

in which
$R^2$ represents hydrogen or alkyl,
$R^3$ represents hydrogen or alkyl and
X denotes a group of the formula $-NR^{12}R^{13}$, $-COR^{14}$, $-SO_2R^{15}$ or $-OR^{16}$, wherein
$R^{12}$ and $R^{13}$ are identical or different and represent hydrogen, alkyl, aryl or aralkyl, where the aryl radicals may be substituted by halogen, cyano, alkyl, alkoxy or trifluoromethyl, or represent a group of the formula $-COR^{14}$, $-SO_2R^{15}$ or $-(CH_2)_c-NR^{12}R^{13}$,
$R^{14}$ denotes hydrogen, or denotes an $-NHR^{17}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino,
$R^{15}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or denotes an $-NR^{10}R^{11}$ group, where $R^{10}$ and $R^{11}$ have the abovementioned meaning,
$R^{16}$ denotes hydrogen, alkyl, aryl, aralkyl or a group of the formula $-CONR^{10}R^{11}$,
$R^{17}$ denotes hydrogen, or denotes cycloalkyl, or denotes alkyl which is optionally substituted by cyano, halogen, trifluoromethyl or trifluoromethoxy, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, and
c denotes a number 1 to 8, or where
$R^{12}$ and $R^{13}$, together with the nitrogen atom, form a ring from the series comprising

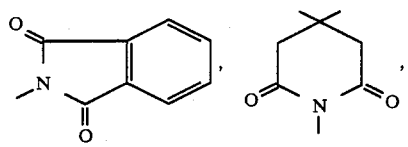

-continued

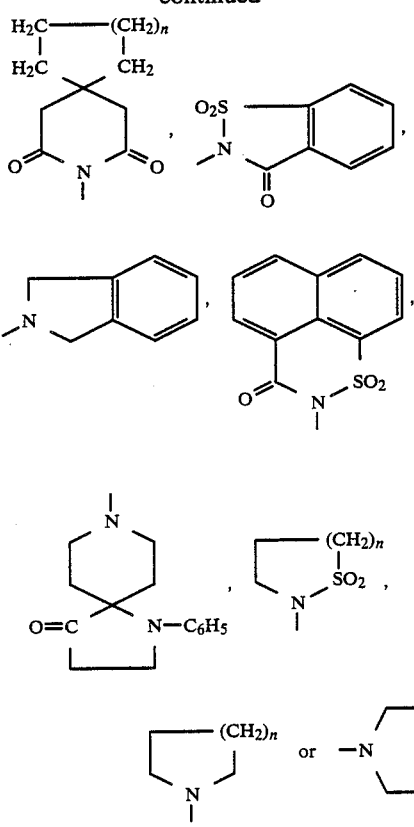

wherein n denotes a number 1 or 2, and

A represents hydrogen or cycloalkyl, or represents alkyl which may be substituted by halogen, hydroxyl, amino, alkylamino, dialkylamino, carbamoyl or sulphamoyl, or represents aryl, heteroaryl, aralkyl, alkoxycarbonyl, alkylsulphonyl, phenylsulphonyl, tolylsulphonyl, benzenesulphonyl, formyl, carbamoyl or sulphamoyl, and the salts thereof, which is characterized in that 8-formyl-aminotetralins of the general formula (Ie)

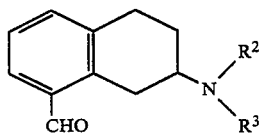

(Ie)

in which $R^2$ and $R^3$ have the abovementioned meaning, are reacted with CH-acidic compounds of the general formula (XIII)

$H_3C-X'$ (XIII)

in which X' has the meaning given for X, or represents nitro, in an inert solvents, if appropriate in the presence of condensation agents, then, if appropriate, functional groups are converted into other functional groups by reduction, hydrolysis, oxidation or reaction with electrophilic reagents, and then, in the case of the preparation of the salts, the products are reacted with the appropriate acid.

The process according to the invention may be illustrated, for example, by the following equation:

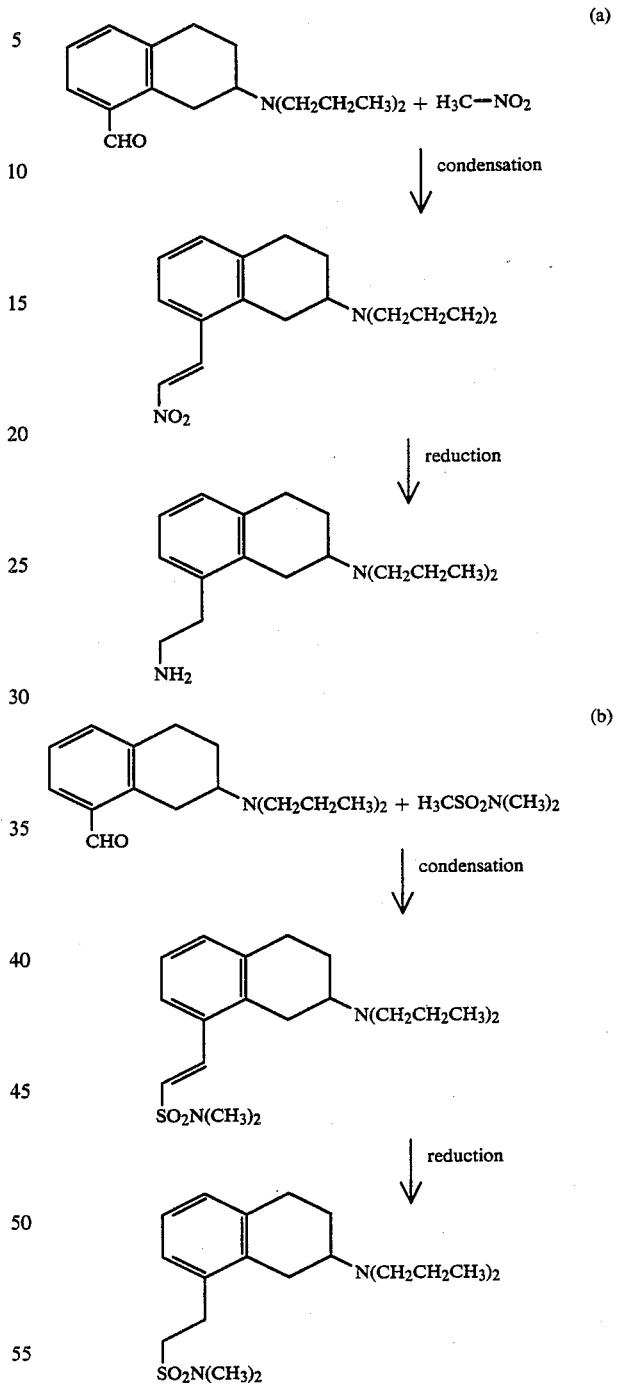

Suitable inert solvents here are those conventional solvents which do not change under the reaction conditions. These preferably include water or alcohols, such as methanol, ethanol, propanol or isopropanol, or ethers such as diethyl ether, butyl methyl ether, dioxane, tetrahydrofuran or glycol dimethyl ether, or halogenated hydrocarbons such as, for example, methylene chloride, chloroform or carbon tetrachloride, or hydrocarbons such as benzene, toluene, xylene or petroleum fractions, or amides such as dimethylformamide or hexamethylphosphoric triamide, or dimethyl sulphoxide or acetic acid. It is likewise possible to use mixtures of the solvents mentioned.

In general, bases are used as condensation agents. These preferably include alkali metal or alkaline earth metal hydroxides, such as sodium hydroxide, potassium hydroxide or barium hydroxide, or alkali metal carbonates such as sodium carbonate or potassium carbonate, or alkali metal alcoholates such as sodium methanolate, sodium ethanolate, potassium methanolate, potassium ethanolate or potassium tert.butanolate, or ammonia, or ammonium acetate, or organic amines such as diethylamine, triethylamine, diisopropylamine, tripropylamine, pyridine, piperidine, morpholine or N,N-dimethylaminopyridine or picoline.

The reaction is generally carried out in a temperature range from 0° C. to +150° C., preferably from +20° C. to 100° C.

The reaction can be carried out at atmospheric, increased or reduced pressure (for example 0.5 to 5 bar). In general, the reaction is carried out at atmospheric pressure.

When carrying out the reaction, the CH-acidic compounds are generally employed in an amount from 0.1 to 100, preferably 0.5 to 50, particularly preferably 1 to 10 moles, relative to 1 mole of the 8-formyl-aminotetralin.

The process according to the invention may be carried out, for example, by mixing and, if appropriate, warming the 8-formyl-aminotetralin with the CH-acidic compound, if appropriate in an inert solvent and if appropriate with bases. The work-up is effected in a conventional fashion by extraction, chromatography and/or crystallization. It is also possible here to carry out the process according to the invention by a phase transfer-catalyzed version.

The conversion of functional groups into other functional groups in the preparation process described above is carried out, depending on the type of functional group, by oxidation, reduction, hydrolysis or by reaction with electrophilic reagents and is intended to be described in detail below.

1. In general, the nitrile group is reduced to the amino group using metal hydrides, preferably using lithium aluminum hydride, aluminum hydride (prepared, for example, by reaction of lithium aluminum hydride with 100% strength sulphuric acid or with aluminum chloride), or mixtures thereof, in inert solvents such as ethers or chlorinated hydrocarbons, preferably in ethers such as, for example, tetrahydrofuran, diethyl ether or dioxane, in a temperature range from −20° C. to +100° C., preferably from 0° C. to +50° C., at atmospheric pressure.

In addition, the reduction is possible by hydrogenation of the nitriles in inert solvents such as alcohols, for example methanol, ethanol, propanol or isopropanol, in the presence of a noble metal catalyst such as platinum, palladium, palladium on animal charcoal, or Raney nickel, in a temperature range from 0° C. to +150° C., preferably from room temperature to +100° C., at atmospheric pressure or at increased pressure.

The reaction may be illustrated by the following equation:

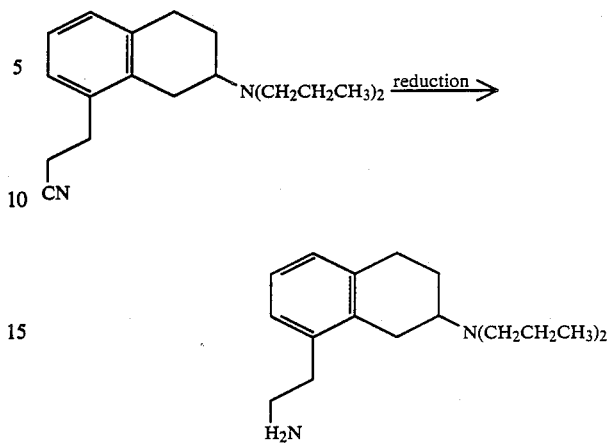

2. In general, carbamates are converted to N-methylamines by reduction using hydrides, preferably using lithium aluminum hydride, in inert solvents such as ethers, hydrocarbons or chlorinated hydrocarbons, preferably in ethers, such as, for example, diethyl ether, tetrahydrofuran or dioxane, in a temperature range from 0° C. to +150° C., preferably from +20° C. to +100° C., at atmospheric pressure.

The reaction may be illustrated by the following equation:

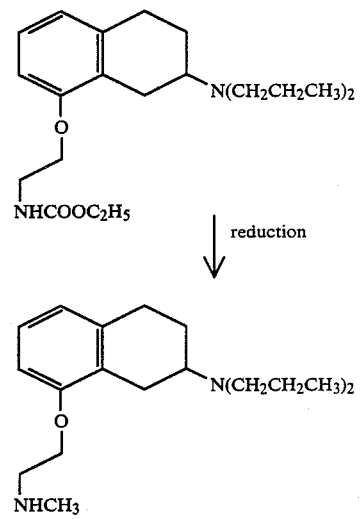

3. In general, alkoxycarbonyl groups are reduced to alcohol groups using hydrides, preferably using lithium aluminum hydride, in inert solvents such as ethers, hydrocarbons or halogenated hydrocarbons, or mixtures thereof, preferably in ethers, such as, for example, diethyl ether, tetrahydrofuran or dioxane, in a temperature range from 0° C. to +150° C., preferably from +20° C. to +100° C., at atmospheric pressure.

The reaction may be illustrated by the following equation

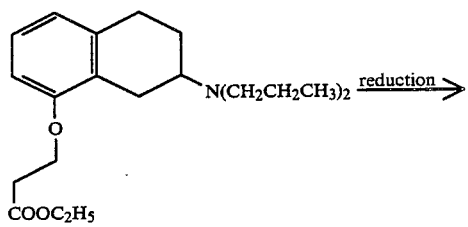

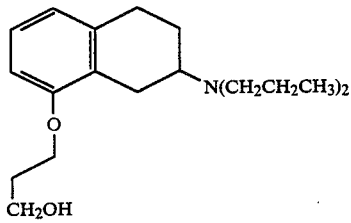

4. In general, the nitrile group is hydrolyzed to the carboxamide group using strong mineral acids, preferably using hydrochloric acid, in inert solvents such as water and/or alcohols, such as, for example, methanol, ethanol, propanol or isopropanol, in a temperature range from 0° C. to +150° C., preferably from +20° C. to +100° C., at atmospheric pressure.

The reaction may be described by the following equation:

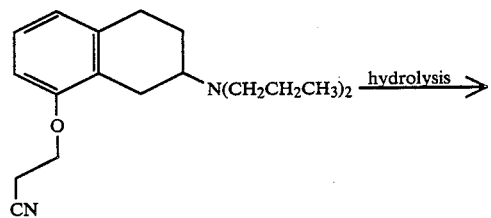

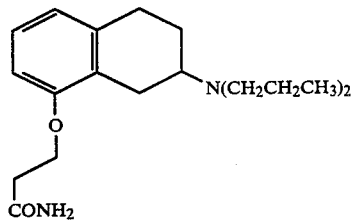

5. A large number of further compounds according to the invention are obtained by reacting NH- or OH-acidic compounds with electrophilic reagents:

(a) In general, amines are converted to carboxamides by reaction with carboxylates in inert solvents such as ethers or hydrocarbons, or their mixtures, preferably in ethers such as, for example, diethyl ether, tetrahydrofuran or dioxane, if appropriate in the presence of bases such as alkali metals, alkali metal hydrides, alkali metal alcoholates or organolithium compounds, preferably in the presence of alkali metals such as, for example, sodium, or alkali metal hydrides such as sodium hydride or potassium hydride, in a temperature range from +20° C. to +150° C., preferably at the boiling temperature of the solvent used, at atmospheric pressure.

In addition, it is possible to prepare the amides using carboxylic acid halides or anhydrides, preferably using carboxylic acid chlorides, in inert solvents such as ethers, hydrocarbons or halogenated hydrocarbons, or mixtures thereof, preferably in ethers such as, for example, diethyl ether or tetrahydrofuran, or halogenated hydrocarbons such as methylene chloride or chloroform, if appropriate in the presence of bases such as alkali metal carbonates, for example sodium carbonate or potassium carbonate, or, organic amines such as, for example, triethylamine or pyridine, in a temperature range from −20° C. to +100° C., preferably from 0° C. to +60° C., at atmospheric pressure.

The reaction may be illustrated by the following equation:

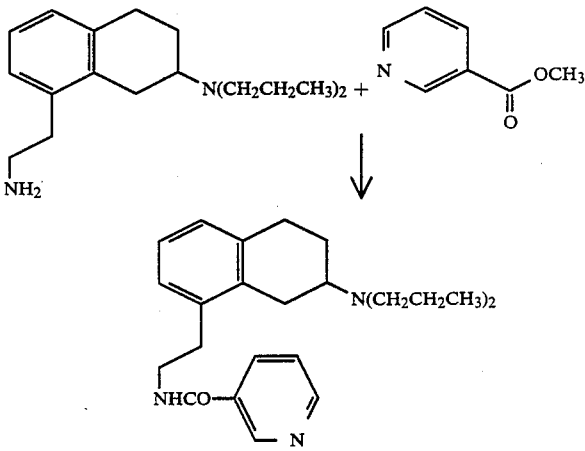

(b) In general, amines are converted to carbamates using carbonates, preferably using asymmetrical carbonates, particularly preferably using carbonates which carry one phenyl ester radical, in inert solvents such as ethers, hydrocarbons or halogenated hydrocarbons, or mixtures thereof, preferably in ethers such as, for example, diethyl ether, tetrahydrofuran or dioxane, in a temperature range from 20° C. to +150° C., preferably from +20° C. to +100° C., at atmospheric pressure.

The reaction may be described by the following equation:

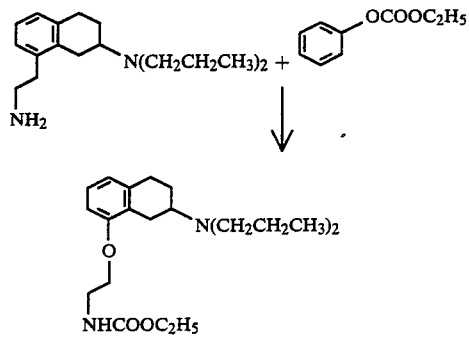

(c) In general, amines are converted to ureas by reaction with isocyanates in inert solvents such as ethers, hydrocarbons or halogenated hydrocarbons or mixtures thereof, preferably in ethers such as, for example, diethyl ether or tetrahydrofuran, or in halogenated hydrocarbons such as, for example, methylene chloride or chloroform, in a temperature range from −20° C. to +150° C., preferably from 0° C. to +100° C., at atmospheric pressure.

The reaction may be described by the following equation:

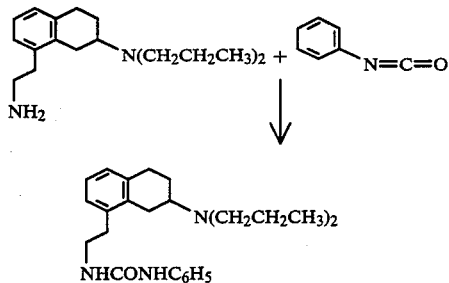

(d) In general, amides are converted to sulphonamides or aminosulphamoyl derivatives using sulphonyl halides or using amidosulphonyl halides, preferably using the corresponding chlorides, in inert solvents such as ethers, hydrocarbons or halogenated hydrocarbons, or mixtures thereof/ preferably in halogenated hydrocarbons such as, for example, methylene chloride or chloroform, if appropriate in the presence of bases such as alkali metal hydroxides, alkali metal carbonates, alkali metal alcoholates or organic amines, preferably using alkali metal hydroxides such as sodium hydroxide or potassium hydroxide, alkali metal carbonates such as, for example, sodium carbonate or potassium carbonate, or organic amines such as triethylamine or pyridine, in a temperature range from −20° C. to +100° C., preferably from 0° C. to +50° C., at atmospheric pressure The reaction may be illustrated by the following equation:

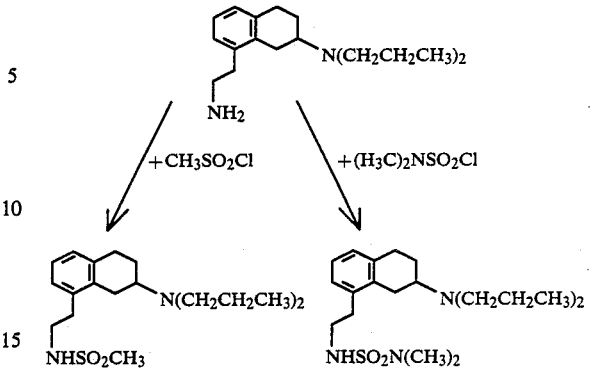

(e) In general, the hydroxyl group is converted to a carbonate by reaction with halogenoformates, preferably with chloroformates, in inert solvents such as ethers, hydrocarbons or halogenated hydrocarbons, preferably in halogenated hydrocarbons such as methylene chloride or chloroform, or in ethers such as diethyl ether or tetrahydrofuran, if appropriate in the presence of bases such as alkali metal hydroxides, alkali metal carbonates or organic amines, preferably in the presence of organic amines such as triethylamine, pyridine, picoline or dimethylaminopyridine, in a temperature range from −20° C. to 100° C., preferably from 0° C. to +30° C., at atmospheric pressure.

The reaction may be illustrated by the following equation:

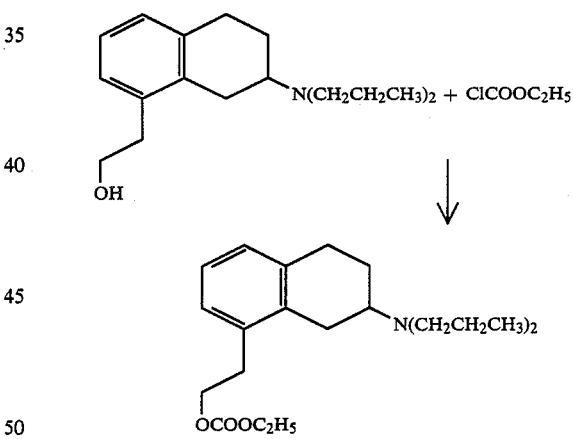

(f) In general, cyclic sulphonamides are prepared by reaction of intramolecular electrophiles in inert dipolar aprotic solvents, preferably in dimethylformamide, hexamethylphosphoric triamide or dimethyl sulphoxide, if appropriate in the presence of bases such as alkali metals, alkali metal hydrides, alkali metal amides, alkali metal alcoholates or organolithium compounds, preferably in the presence of alkali metal hydrides such as sodium hydride or potassium hydride, or alkali metal amides such as sodium amide or lithium diisopropylamide, if appropriate in the presence of catalytic amounts of an alkali metal iodide, for example sodium iodide or potassium iodide, in a temperature range from −20° C. to +100° C., preferably from 0° C. to +50° C., at atmospheric pressure.

The reaction may be illustrated by the following equation:

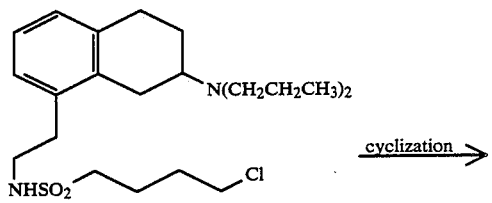

cyclization →

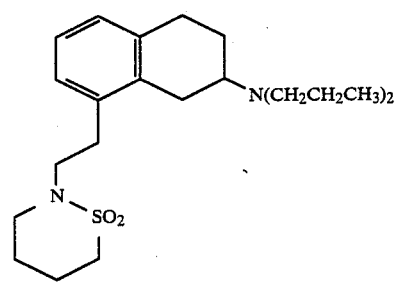

6. A further variation of the process according to the invention with respect to the functional groups in $R^1$ is given by the reduction of the double bond in $R^1$, nitro groups ($X'=NO_2$) which are present simultaneously being reduced to amino groups. The reduction is generally carried out using metal hydrides, preferably using lithium aluminum hydride, aluminum hydride (prepared, for example, by reaction of lithium aluminum hydride with sulphuric acid and aluminum chloride), sodium borohydride, lithium borohydride, or mixtures thereof, in inert solvents such as ethers or chlorinated hydrocarbons, preferably in ethers such as, for example, tetrahydrofuran, dioxane or diethyl ether, in a temperature range from $-20°$ C. to $+100°$ C., preferably from $0°$ C. to $+80°$ C., at atmospheric pressure.

It is likewise possible to carry out this reduction by hydrogenation in inert solvents such as alcohols, for example methanol, ethanol or isopropanol, in the presence of catalysts such as platinum, platinum oxide, palladium, palladium on animal charcoal, or Raney nickel, if appropriate in the presence of acids such as hydrochloric acid, acetic acid, trichloroacetic acid or trifluoroacetic acid, in a temperature range from $0°$ C. to $+200°$ C., preferably from $+20°$ C. to $+100°$ C., at atmospheric pressure or superatmospheric pressure.

The reaction may be iLlustrated by the following equation:

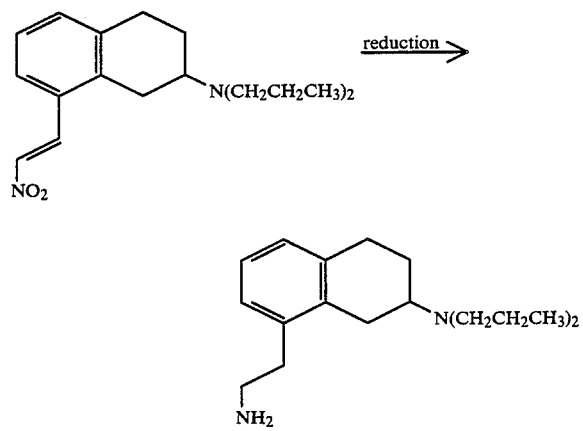

Compounds formula (I) with $R=O\ (CH_2)_aX$ (in which a and X have the specified meaning) can be obtained from the corresponding 8-hydroxy-2-alkylamino-tetralins. The 8-hydroxy-2-alkylamino-tetralins are known (EP-A 41 488) or can be prepared from the corresponding halogen-compounds of formula (I).

The 8-hydroxy-2-alkylamino-tetralins are reacted under alkylation conditions (which are known per se) with compounds of the formula $$Y-(CH_2)_a-X$$

in which
Y represents $-Cl$, $-Br$ or $-OSO_2$-alkyl ($C_1$ to $C_4$) and
X and a have the above meaning.

The substances of the general formula (I) according to the invention have a high affinity for cerebral 5-hydroxytryptamine receptors of the 5-HT$_1$-type. Agonistic, partially agonistic or antagonistic actions on the serotonin receptor are connected with this, against which the known substances have purely agonistic properties.

The high-affinity ligands, described in the present invention, for the serotonin-1 receptor thus represent better active compounds for combating diseases which are characterized by disturbances to the serotoninergic system, particularly when involvine receptors which have a high affinity to 5-hydroxytryptamine (5-HT$_1$ type). They are therefore suitable for the treatment of diseases of the central nervous system, such as anxiety, tension and depression, sexual dysfunctions caused by the central nervous system, and insomnia. In addition, they are suitable for eliminating congnitive deficits, for improving learing and memory performance and for treatment of Alzheimer's disease. In addition, these active compounds are also suitable for modulation of the cardiovascular system. They also engage in the regulation of the cerebral blood supply, and thus represent effective agents for combating migraine. The compounds according to the invention can likewise be employed for combating pain. They are also suitable for combating diseases of the intestinal tract, which are characterized by disturbances of the serotoninergic system.

The new active compounds can be converted in a known manner into the customary formulations, such as tablets, dragees, pills, granules, aerosols, syrups, emulsions, suspensions and solutions, using inert non-toxic, pharmaceutically suitable excipients or solvents. The therapeutically active compound should in each case be present here in a concentration of about 0.5 to 90% by weight of the total mixture, that is to say in amounts which suffice to achieve the dosage range indicated.

The formulations are prepared, for example, by extending the active compounds with solvents and/or excipients, optionally with the use of emulsifiers and/or dispersing agents, and, for example, when using water as a diluent, organic solvents can optionally be used as auxiliary solvents.

Examples of auxiliary substances which may be mentioned are: water, non-toxic organic solvents, such as paraffins (for example petroleum fractions), vegetable oils (for example groundnut oil/sesame oil), alcohols (for example ethyl alcohol and glycerol), excipients, such as, for example, ground natural minerals (for example kaolins, clays, talc and chalk), ground synthetic minerals (for example highly disperse silica and silicates) and sugars (for example sucrose, lactose and glucose), emulsifiers (for example polyoxyethylene fatty acid esters), polyoxyethylene fatty alcohol ethers (for example lignin-sulphite waste liquors, methylcellulose, starch and polyvinylpyrrolidone) and lubricants (for example magnesium stearate, talc, stearic acid and sodium sulphate).

Administration is effected in the customary manner, preferably orally or parenterally, particularly perlingually or intravenously. In the case of oral use, the tablets can, of course, also contain, in addition to the excipients mentioned, additives such as sodium citrate, calcium carbonate and dicalcium phosphate, together with various additional substances, such as starch, preferably potato starch, gelatine and the like. Furthermore, lubricants, such as magnesium stearate, sodium lauryl sulphate and talc, can be used concomitantly when making tablets. In the case of aqueous suspensions, the active compounds can be mixed with various flavor-improving agents or colorants in addition to the abovementioned auxiliary substances.

In the case of parenteral use, solutions of the active compounds, using suitable liquid excipients, can be employed.

In general, it has proved advantageous, in the case of intravenous administration, to administer amounts of about 0.001 to 1 mg/kg, preferably about 0.01 to 0.5 mg/kg, of body weight to achieve effective results, and in the case of oral administration, the dosage is about 0.01 to 20 mg/kg, preferably 0.1 to 10 mg/kg of body weight.

Nevertheless, it may be necessary, under certain circumstances, to deviate from the amounts mentioned, and in particular to do so as a function of the body weight or of the nature of the administration method, of the individual behavior towards the medicament, the nature of its formulation, and the time or interval over which the administration takes place. Thus, it can in some cases be sufficient to manage with less than the abovementioned minimum amount, whereas in other cases the upper limit mentioned must be exceeded. In the case of administration of larger amounts, it may be advisable to divide these into several individual administrations over the course of the day.

PREPARATION EXAMPLES

Example 1

2-Dipropylamino8-chloro-1,2,3,4-tetrahydronaphthalene

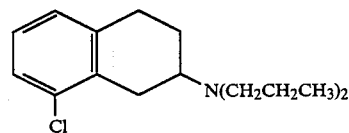

700mg (2.8 mmol) of 2-dipropylamino-8-amino-1,2,3,4-tetrahydronaphthalene were dissolved in 2.5 ml of water and 1.14 ml (13.7 mmol) of 37% strength hydrochloric acid. A solution of 195 mg of sodium nitrite and 0.45 ml of water were added dropwise to this solution at an internal temperature of 0° C. The solution was subsequently stirred for 15 minutes at 0° C.

In the meantime, 396 mg (4 mmol) of copper(I) chloride were dissolved in 1.6 ml of water, and the solution was cooled to 0° C. The reaction solution above was carefully added dropwise to this solution, and the batch was warmed for 30 minutes at +95° C. until the evolution of nitrogen had ceased.

The reaction mixture was neutralized using aqueous potassium bicarbonate solution and extracted with dichloromethane. The organic phase was dried over sodium sulphate and the solvent was separated off. The residue was purified by means of column chromatography on silica gel. Dichloromethane/methanol, 20:2, was used as eluent.

Yield: 74% of theory (oily product)

$R_f$: 0.64.

The base was precipitated as the hydrochloride from a solution of petroleum ether using ethereal hydrogen chloride solution. The hydrochloride was a very hygroscopic, colorless, crystalline product.

Example 2

Process version A:

2-Dipropylamino-8-bromo-1,2,3,4-tetrahydronaphthalene

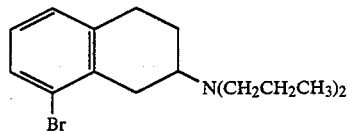

The reaction could be carried out analogously to the reaction for 2-dipropylamino-8-chloro-1,2,3,4-tetrahydronaphthalene (Example 1), employing copper(I) bromide and 47% strength hydrobromic acid.

Yield: 32% of theory (oily product)

$R_f$: 0.73 (dichloromethane/methanol 20:2).

The base was precipitated as the hydrochloride from a solution of petroleum ether using ethereal hydrogen chloride solution. The hydrochloride was a very hygroscopic, colorless, crystalline product.

Process version B:

1. 8-Bromo-2-tetralone

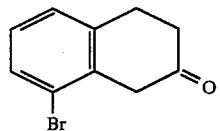

83.5 g of aluminum chloride (0.63 mmol) were introduced into 1.8 liters of methylene chloride at 0°–+5° C. 105 g (0.49 mole) of 2-bromophenyl-acetyl chloride (dissolved in 200 ml of methylene chloride) were added dropwise at 0°–+5° C. over 30 minutes. After stirring for 30 minutes at 0°–+5° C., 50 g of ethylene were passed in at such a rate that the reaction temperature did not exceed +10° C. The mixture was stirred for a further 2 hours at 20°–+25° C. The aluminum complex was decomposed by careful addition of 500 ml of ice water, the phases were separated, and the aqueous phase was extracted with 250 ml of methylene chloride. The title compound was obtained from the dried methylene chloride phase in a yield of 109 g as a yellow oil (content according to GC 97%) and employed without further purification.

2. 8-Bromo-2-dipropylamino-1,2,3,4-tetrahydronaphthalene (a) Enamine synthesis: 385 g (1.71 mole) of 8-bromo-2tetralone and 165 g of propylamine (2.8 mole) were stirred under reflux for 2 hours on a water separator in 700 ml of benzene, in the presence of 1.5 g of Amberlyst 15 ion exchange resin. The ion exchange resin was filtered off and the filtrate was concentrated under reduced pressure. The residue (437 g) which remained was employed as a crude product in the reductive alkylation.

(b) Reductive alkylation: 437 g of crude enamine (a) were initially introduced into 3 liters of propionic acid at 0°–+5° C. 310 g of sodium borohydride were added in portions at 0°–+10° C. When the addition was complete, the reaction temperature was increased slowly to +50° C. and maintained for 2 hours. The reaction temperature was subsequently increased to +120° C. and maintained for 3 hours. The cooled reaction solution was diluted with 10 liters of ice water and rendered weakly alkaline by addition of sodium hydroxide solution (45% strength). 320 g of the final product (boiling point 128°–135° C.; 0.07 mm) were obtained by means of extraction with chloroform and fractional distillation (GC 90% pure).

The secondary amine 8-bromo-2-propylamino-tetrahydronaphthalene is obtained if the reaction is interrupted after stirring for 2 hours at +50° C. and worked-up as described.

Example 3

Process version A:

2-Dipropylamino-8-cyano-1,2,3,4-tetrahydronaphthalene

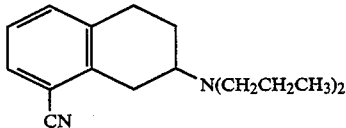

6.0 g (24 mmol) of 2-dipropylamino-8-amino-1,2,3,4tetrahydronaphthalene were dissolved in 36 g (120 mmol) of 33% strength sulphuric acid under nitrogen. A solution of 1.7 g (24 mmol) of sodium nitrite in 5 ml of water was then added dropwise at 0° C. to a maximum of +5° C. The reaction solution was subsequently stirred for a further 30 minutes at the same temperature and then added dropwise to a solution, warmed to 50° C., of 2.9 g (32 mmol) of copper(I) cyanide, 8.7 g (177 mmol) of sodium cyanide and 39 ml of water. The batch was then stirred for a further 1 hour at 50° C. until the evolution of nitrogen had ceased.

The batch was subsequently stirred in 500 ml of ice water and the mixture was adjusted to pH 10 using 2 N sodium hydroxide solution. The mixture was then extracted with dichloromethane and the organic phase was washed with water until neutral. The solution was dried over sodium sulphate and the solvent was removed by distillation. The residue was purified by column chromatography on silica gel. Toluene/methanol, 85:15, was used as eluent.

Yield: 48% of theory (oil)

$R_f$: 0.63 (toluene/methanol 83:17)

Process version B:

152 g of 8-bromo-2-dipropylamino-1,2,3,4-tetrahydronaphthalene (Example 2) (0.49 mole) and 66 g of copper(I) cyanide were stirred for 6 hours at 150° C. in 450 ml of dimethylformamide. The cooled reaction batch was introduced into a mixture of 150 ml of ethylenediamine and 450 ml of $H_2O$, and stirred for 1 hour at room temperature. The crude product, obtained by extraction with ethyl acetate, was subjected to fractional distillation. The product was obtained as a colorless oil (boiling point 140°–150° C.; 0.1 mm) in a yield of 73 g (GC 95%).

Example 4

2-Dipropylamino-8-(3-butyl-ureido)-1,2,3,4-tetrahydronaphthalene

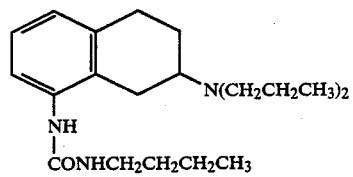

0.7 g (2.8 mmol) of 2-dipropylamino-8-amino-1,2,3,4-tetrahydronaphthalene were dissolved in 3 ml of toluene. 0.34 g (3.4 mmol) of butyl isocyanate were added to the solution and the mixture was stirred for 17 hours at room temperature.

The solvent was subsequently removed by distillation in vacuo and the residue was purified by column chromatography on silica gel. Ethyl acetate/methanol/triethylamine, 20:1:0.1, was used as eluent.

Yield: 51% of theory (oily substance)

$R_f$: 0.51

After dissolving in petroleum ether, it was possible to convert the base into the hydrochloride by dropwise addition of ethereal hydrogen chloride solution. The hydrochloride was a colorless, slightly hygroscopic, crystalline substance.

Example 5

2-Dipropylamino-8-formamido-1,2,3,4-tetrahydronaphthalene

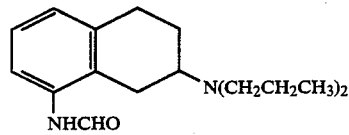

1.06 g (10.4 mmol) of acetic anhydride and 0.48 g (10.4 mmol) of formic acid were combined and warmed for 3.5 hours at 50° C. After cooling, a solution of 0.85 g (3.5 mmol) of 2-dipropylamino-8-amino-1,2,3,4-tetrahydronaphthalene and 5 ml of formic acid was added dropwise and the batch was stirred for 17 hours at room temperature.

The solvent was subsequently removed by distillation in vacuo and the residue was dissolved in dichloromethane. The solution was then washed with aqueous potassium bicarbonate solution and dried over sodium sulphate. The solvent was subsequently removed by distillation.

Example 6

2-Dipropylamino-8-carbamoyl-1,2,3,4-tetrahydronaphthalene

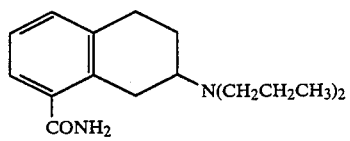

1.0 g (4 mmol) of 2-dipropylamino-8-cyano-1,2,3,4-tetrahydronaphthalene and 0.5 g (8 mmol) of potassium hydroxide in 10 ml of tert.butanol were refluxed for 6 hours under nitrogen. After cooling, the reaction solution was diluted with 20 ml of saturated sodium chloride solution and extracted with dichloromethane. The organic phase was dried using sodium sulphate and the solvent was removed by distillation in vacuo. The residue was crystallized from 10 ml of diisopropyl ether.

Yield: 56% of theory (beige powder)
Boiling point: 105°–106° C.
$R_f$: 0.25 (silica gel; dichloromethane/methanol 75:25)

Example 7

2-Dipropylamino-1,2,3,4-tetrahydronaphthalene-8-carboxylic acid

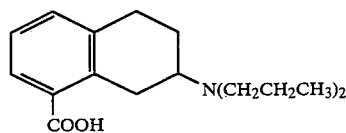

256 mg (1 mmol) of 2-dipropylamino-8-cyano-1,2,3,4-tetrahydronaphthalene, 132 mg (2 mmol) of potassium hydroxide and 36 mg (2 mmol) of water in 1 ml of ethylene glycol were stirred for 20 hours at +150° C. under nitrogen. After cooling, the reaction solution was diluted with 6 ml of water and extracted with dichloromethane. The aqueous phase was adjusted to pH 1–2 using 2.75 ml of 1 N hydrochloric acid, and was then extracted again with dichloromethane. The aqueous phase was subsequently adjusted to pH 5 using 25% strength ammonia solution. The water was then removed by distillation in vacuo and the residue was dried at +50° C. and a vacuum of 0.05 mbar until the weight remained constant. The residue was then dissolved in absolute tetrahydrofuran. After the insoluble salts had been filtered off, the solution was freed of solvent in vacuo. The reaction product remained as a residue, as a virtually colorless oil.

Yield: 44% of theory
$R_f$: 0.67 (silica gel; dichloromethane/methanol/25% strength ammonia solution 67:27:6)

Example 8

2-Dipropylamino-8-ethoxycarbonyl-1,2,3,4-tetrahydronaphthalene

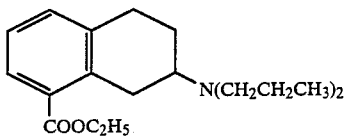

300 mg (1.1 mmol) of 2-dipropylamino-1,2,3,4-tetrahydronaphthalene-8-carboxylic acid were stirred at room temperature in 30 ml of absolute ethanol and 3 ml of a solution of hydrogen chloride in diethyl ether (190 mg/ml), until the reaction was complete. The solvent was subsequently removed by distillation in vacuo and the residue was dissolved in 10 ml of dichloromethane. The solution was washed once with 0.1 N sodium hydroxide solution and twice with water, and dried over sodium sulphate. The solvent was then removed by distillation in vacuo. The reaction product remained as a virtually colorless oil.

Yield: 64% of theory
$R_f$: 0.97 (silica gel; dichloromethane/methanol/25% strength ammonia solution 67:27:6)

Example 9

2-Dipropylamino-8-formyl-1,2,3,4-tetrahydronaphthalene

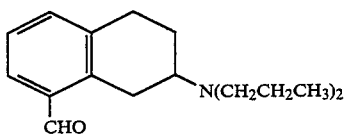

3.75 g (154.4 mmol) of magnesium powder were initially introduced into 100 ml of dry tetrahydrofuran under argon. Several drops of iodoethane were added, and a solution of 31.9 g (103 mmol) of 2-dipropylamino-8-bromo-1,2,3,4-tetrahydronaphthalene and 20 ml of absolutely dry tetrahydrofuran were then added dropwise at 0° C. The mixture was stirred for 3 hours at +60° C. Cooling to room temperature was then effected, and 12.8 g (113.3 mmol) of N-formylpiperidine were then added dropwise at this temperature. The mixture was stirred for a further 30 minutes at room temperature and then hydrolyzed using 3 N hydrochloric acid. The mixture was then adjusted to pH 12 and extracted with ethyl acetate. Chromatography was carried out using cyclohexane/ethyl acetate/triethylamine, 80:19:1, over silica gel 60, 63–200 μm.

Yield: 65.5% of theory (oil)
$R_f$: 0.342 (diisopropyl ether/triethylamine 99:1)

---

The residue was purified by column chromatography on aluminum oxide 90 (aluminum oxide from Merck, activity II–III). Cyclohexane/methanol/triethylamine, 20:0.5:0.1, was used as eluent.

Yield: 42% of theory (crystalline substance)
$R_f$: 0.62

After dissolving in diethyl ether, the base could be converted into the hydrochloride by dropwise addition of an ethereal hydrogen chloride solution. The hydrochloride was a colorless, very hygroscopic, crystalline substance.

Example 10

2-Dipropylamino-8-hydroxymethyl-1,2,3,4-tetrahydronaphthalene

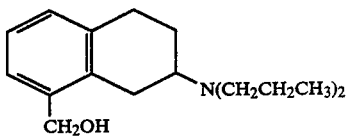

15 mg (0.4 mmol) of lithium aluminum hydride were suspended in 2 ml of diethyl ether under nitrogen. A solution of 210 mg (0.7 mmol) of 2-dipropylamino-8-ethoxycarbonyl-1,2,3,4-tetrahydronaphthalene in 1 ml of diethyl ether was carefully added dropwise to the suspension. The batch was subsequently stirred for a further 5 hours at room temperature.

First 5 mg (0.05 mmol) of ethyl acetate, then 15 mg of water, subsequently 20 mg of 15% strength sodium hydroxide solution and finally a further 50 mg of water were then added dropwise and stirred for 0.5 hours in each case. The batch was then diluted with 3 ml of diethyl ether. The precipitate was filtered off and the filtrate was washed with water and freed of solvent. The oily residue was dried in a vacuum of 0.05 mbar and at a temperature of 50° C. until the weight remained constant.

Yield: 71% of theory
$R_f$: 0.28 (silica gel; toluene/methanol 85:15)

Example 11

8-Acetylamino-2-dipropylamino-1,2,3,4-tetrahydronaphthalene

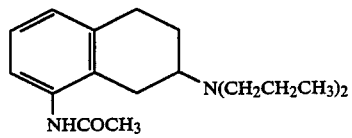

24 g (0.094 mol) of 8-cyano-2-dipropylamino-1,2,3,4-tetrahydronaphthalene were initially introduced into 100 ml tetrahydrofuran (absolute); 4.5 g of lithium aluminum hydride (0.12 mol) were added in portions at +20°–+30° C. After stirring for 2 hours under reflux, the excess lithium aluminum hydride was decomposed by addition of water and sodium hydroxide. The precipitated inorganic solid was filtered off under suction and washed with 50 ml of tetrahydrofuran. The crude product (25 g) remaining after drying and concentrating the filtrate was dissolved in 200 ml of methylene chloride, and 10 g of triethylamine were added. After addition of 0.2 g of dimethylaminopyridine as acylation catalyst, 1 g of acetic anhydride was added dropwise at +20°–+25° C. After a stirring for further twelve hours at +20°–+25° C., the reaction solution was washed with sodium bicarbonate and water, dried and concentrated. The resultant crude product (30 g) was recrystallized from hexane/ethyl acetate (10:1). The product was isolated as a solid in a yield of 75% of theory.

Melting point: 99°–100° C.

Example 12

2-Dipropylamino-8-aminomethyl-1,2,3,4-tetrahydronaphthalene

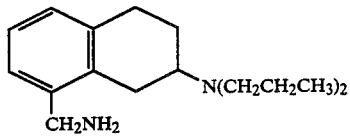

10.6 g (35 mmol) of 2-dipropylamino-8-acetamidomethyl-1,2,3,4-tetrahydronaphthalene in 100 ml of ethanol and 23.1 g (350 mmol) of potassium hydroxide were heated to a gentle reflux for 24 h at 90° C. under nitrogen. The batch was subsequently stirred into 1 liter of ice water and the mixture was extracted with dichloromethane. The organic phase was washed with water and dried over sodium sulphate. The solvent was removed by distillation in vacuo. The reaction product, remaining as a residue, was purified by column chromatography on silica gel using methanol/triethylamine, 95:5, as eluent.

Yield: 59% of theory (oil)
$R_f$: 0.62

Example 13

2-Dipropylamino-8-aminomethyl-1,2,3,4-tetrahydronaphthalene hydrochloride

The compound of Example 12 was dissolved in ether. By dropwise addition of ethereal hydrogen chloride solution, the hydrochloride was precipitated and was then filtered off under suction and dried in vacuo at room temperature.

Yield: 3.6 g
Melting point: 97°–100° C.

Example 14

2-Dipropylamino-8-methylsulphonamido-methyl-1,2,3,4-tetrahydronaphthalene

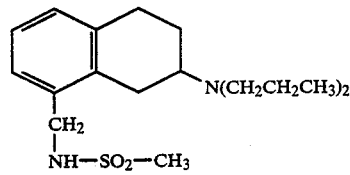

1.6 g (6 mmol) of 2-dipropylamino-8-aminomethyl-1,2,3,4-tetrahydronaphthalene were dissolved in 16 ml of dichloromethane under nitrogen. 0.7 g (6 mmol) of methanesulphonyl chloride was then added dropwise at a maximum of 25° C. The reaction solution was then stirred for 18 hours at room temperature. 16 ml of water were then added. The mixture was adjusted to pH 10 using 1 N sodium hydroxide solution. The organic phase was separated off and washed with water. After drying over sodium sulphate, the solvent was removed by distillation in vacuo. The residue was purified by column chromatography on silica gel using diisopropyl ether/isopropanol/triethylamine, 65:70:5, as eluent.

Yield: 76% of theory (oil)
$R_f$: 0.55

Example 15

2-Dipropylamino-8-butylsulphonamidomethyl-1,2,3,4-tetrahydronaphthalene

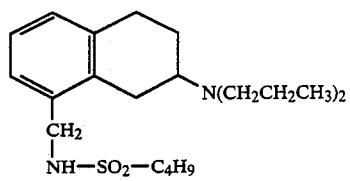

1.6 g (6 mmol) of 2-dipropylamino-8-aminomethyl1,2,3,4-tetrahydronaphthalene were dissolved in 16 ml of dichloromethane under nitrogen. 0.9 g (6 mmol) of butanesulphonyl chloride was then added dropwise at a maximum of +25° C. The reaction solution was then stirred for 18 hours at room temperature. 16 ml of water were then added. The mixture was adjusted to pH 10 using 1 N sodium hydroxide solution. The organic phase was separated off and washed with water. After drying over sodium sulphate, the solvent was removed by distillation in vacuo. The residue was purified by column chromatography on silica gel using diisopropyl ether/triethylamine, 99.5:0.5, as eluent. Further purification was achieved by dissolving the base in ether and converting to the hydrochloride by dropwise addition to an ethereal hydrogen chloride solution. After addition of water and separation of the organic phase, the base was liberated again by addition of sodium hydroxide solution and isolated by extraction with ether.

Yield: 49% of theory (oil)

$R_f$: 0.10 (silica gel; diisopropyl ether/triethylamine 99.5:0.5 )

Example 16

2-Dipropylamino-8-ethoxycarbonylamido-methyl-1,2,3,4-tetrahydronaphthalene

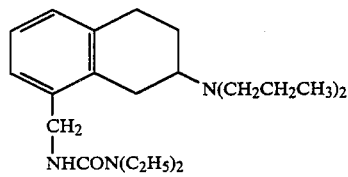

1.6 g (6 mmol) of 2-dipropylamino-8-aminomethyl-1,2,3,4-tetrahydronaphthalene were dissolved in 16 ml of diethyl ether under nitrogen. 0.58 ml of ethyl chloroformate was added dropwise, with cooling, at a maximum of +5° C. The batch was subsequently stirred for a further 1 h at +5° C. and then stirred into ice water. The aqueous phase was adjusted to pH 10 using 1 N sodium hydroxide solution and then extracted with ether. The organic phase now obtained was washed with water and dried over sodium sulphate. The solvent was removed by distillation and the remaining residue was purified by column chromatography on silica gel. Diisopropyl ether/triethylamine, 99.5:0.5, was used as eluent.

$R_f$: 0.20

Example 17

2-Dipropylamino-8-ethoxycarbonylamido-methyl-1,2,3,4-tetrahydronaphthalene hydrochloride The free base of the compound of Example 16 was converted into the hydrogen chloride, after dissolving in diisopropyl ether, using ethereal hydrogen chloride solution. The very hygroscopic hydrochloride was filtered off under suction and dried in vacuo.

Yield: 18% of theory

Example 18

2-Dipropylamino-8-(3,3-diethylureido)methyl-1,2,3,4-tetrahydronaphthalene

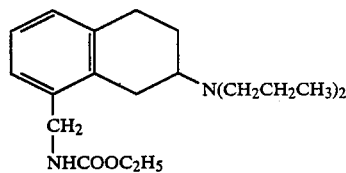

1.6 g (6 mmol) of 2-dipropylamino-8-aminomethyl-1,2,3,4-tetrahydronaphthalene were dissolved in 16 ml of dichloromethane under nitrogen. 0.81 g (6 mmol) of diethylcarbamoyl chloride was then added dropwise at a maximum of +25° C. The batch was then stirred for 26 h at room temperature. The batch was then stirred into 160 ml of ice water. The mixture was adjusted to pH 9 using 1 N sodium hydroxide solution and extracted with dichloromethane. The organic phase was washed with water and dried over sodium sulphate. The solvent was subsequently removed by distillation. The residue was purified by column chromatography. Diisopropyl ether/isopropanol/triethylamine, 80:19.5:0.5, was used as eluent. The final product could be crystallized from petroleum ether 30–50 and was dried at +40° C. in vacuo.

Yield : 64% of theory

Melting point: 86°–87° C.

$R_f$: 0.42

Example 19

2-Dipropylamino-8-ureidomethyl-1,2,3,4,-tetrahydronaphthalene

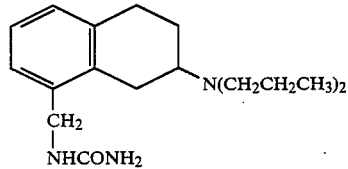

2.6 g (10 mmol) of 2-dipropylamino-8-aminomethyl-1,2,3,4-tetrahydronaphthalene were dissolved in 22 ml of 1 N hydrochloric acid under nitrogen. A solution of 0.81 g (10 mmol) of potassium cyanate and 6 ml of water was subsequently added dropwise at a maximum of +25° C., and the batch was allowed to react for 4 h at room temperature. 20 ml of diethyl ether were then added. The aqueous phase was separated off and adjusted to pH 9 using 1 N sodium hydroxide solution. The precipitated reaction product was filtered off under suction and dried at +40° C. in vacuo. The product was purified by recrystallization from methanol.

Yield: 38% of theory
Melting point: 182.5°–183.5° C.
R$_f$: 0.55

Example 20

2-Dipropylamino-8-(3-methylureido)methyl-1,2,3,4-tetrahydronaphthalene

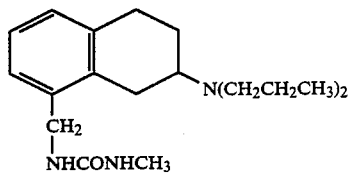

1.6 g (6 mmol) of 2-dipropylamino-8-aminomethyl-1,2,3,4-tetrahydronaphthalene were dissolved in 16 ml of toluene under nitrogen. 0.34 g (6 mmol) of methyl isocyanate was added dropwise at a maximum of +25° C. The batch was subsequently stirred for a further 1.5 h at room temperature. The reaction product which crystallized out was then filtered off under suction and dried at +40° C. in vacuo.

Yield: 65% of theory
R$_f$: 0.45

Example 21

2-Dipropylamino-8-formamidomethyl-1,2,3,4,-tetrahydronaphthalene

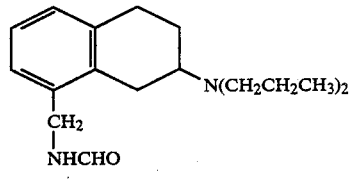

2.04 ml (21.5 mmol) of acetic anhydride and 0.86 ml (22.8 mmol) of formic acid were stirred for 2 h at +60° C. under nitrogen. After cooling to room temperature, 2.6 g (10 mmol) of 2-dipropylamino-8-aminomethyl-1,2,3,4-tetrahydronaphthalene were added dropwise at a maximum of +25° C. After 15 minutes post-reaction, 5 ml of ether were added. The batch was subsequently stirred for a further 18 h at room temperature and then diluted with 20 ml of ether and 20 ml of water. The aqueous phase was adjusted to pH 9 using 1 N sodium hydroxide solution and extracted with ether. The organic phase now obtained was washed with water and dried over sodium sulphate, and the solvent was removed by distillation. The residue was recrystallized from petroleum ether 60–80.

Yield: 46% of theory
Melting point: 74.5°–75.5° C.

Example 22

2-Dipropylamino-8-(2-hydroxyethoxy)-1,2,3,4-tetrahydronaphthalene hydrochloride

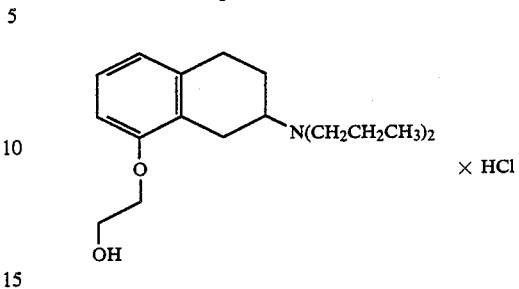

0.7 g (23 mmol) of sodium hydride (80% in paraffin) was initially introduced into 5 ml of diethylene glycol dimethyl ether. A solution of 4.9 g (20 mmol) of 2-dipropylamino-8-hydroxy-1,2,3,4-tetrahydronaphthalene and 20 ml of diethylene glycol dimethyl ether was then added dropwise at +25° C. The mixture was stirred for 30 minutes at +50° C. After cooling to +25° C., 2.5 g (20 mmol) of 2-bromoethanol were added dropwise. The mixture was stirred for 2 h at +100° C. The cooled batch was poured into water and extracted twice with ethyl acetate. The organic phase was dried over sodium sulphate and evaporated. Unreacted starting material was removed by chromatography using chloroform over basic aluminum oxide, activity I. 700 mg of a viscous oil were subsequently obtained by chromatography over silica gel 60, 40–63 μm, using diisopropyl ether/ethanol 3:2. The oil was dissolved in ether and the hydrochloride was precipitated using ethereal hydrochloric acid. The product was extracted with water and washed once more with ether. Methylene chloride was subsequently added and the pH adjusted to 11 using ammonia. The organic phase was separated off, dried using sodium sulphate and filtered. The hydrochloride was again precipitated using ethereal hydrochloric acid. The hydrochloride was evaporated to dryness, and a glassy residue was obtained.

Yield: 6% of theory
R$_f$: 0.392 (diisopropyl ether : ethanol 3:2)

Example 23

2-Dipropylamino-8-carbamoylmethoxy-1,2,3,4-tetrahydronaphthalene

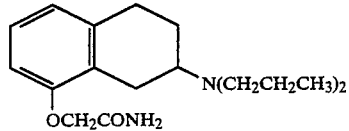

0.35 g (11 mmol) of an 80% dispersion of sodium hydride in oil was washed with petroleum ether and then suspended in diglyme under nitrogen. A solution of 2.50 g (10 mmol) of 2-dipropylamino-8-hydroxy-1,2,3,4-tetrahydronaphthalene and 5.9 ml of diglyme was added dropwise within 30 minutes at +20°–+25° C. with gentle cooling. The batch was subsequently stirred for a further 30 minutes and then warmed at +50° C. for 15 min. 0.94 g (10 mmol) of chloroacetamide was then added in portions at +20°–+25° C. The batch was then warmed at +135° C. for 1 h and, after cooling, stirred into 100 ml of ice water. The precipitate was filtered off under suction and dried at +40° C. in vacuo. The crude substance was purified by recrystallizing twice from isopropanol.
Yield: 50% of theory
Melting point: 132°–132.5° C.
$R_f$: 0.43 (silica gel; toluene/methanol 70:30)

Example 24

2-Dipropylamino-8-(2-aminoethoxy)-1,2,3,4-tetrahydronaphthalene

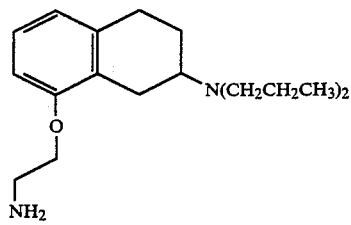

12.5 g (0.328 mol) of lithium aluminum hydride were initially introduced into 200 ml of absolute ether under nitrogen. A suspension of 25 g (0.082 mol) of 2-dipropylamino -8-(carbonamido-methoxy)-1,2,3,4-tetrahydronaphthalene in 500 ml of absolute ether was added to this in small portions. The mixture was stirred for 4 h at 25° C. and then carefully decomposed using water. The mixture was filtered under suction and the residue was washed thoroughly 3 times with ether. The ether phase was separated off, dried over sodium sulphate and then evaporated to dryness. Chromatography was then effected over silica gel 60, 40–63 μm, using isopropanol/triethylamine 95:5.
Yield: 73.6% of theory
$R_f$: 0.208

Example 25

2-Dipropylamino-8-(2-methanesulphonamido-ethoxy)-1,2,3,4-tetrahydronaphthal

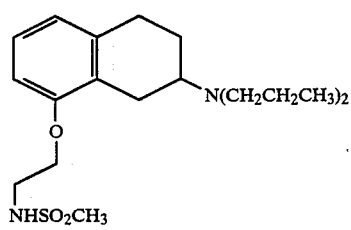

1.45 g (5 mmol) of 2-dipropylamino-8-(2-aminoethoxy)-1,2,3,4-tetrahydronaphthalene and 1.38 g (10 mmol) of potassium carbonate were initially introduced into 20 ml of toluene. 0.63 g (5.5 mmol) of methanesulphonyl chloride was then added dropwise, and the mixture was subsequently stirred for 3 h at room temperature. The mixture was then filtered and evaporated. The residue obtained was stirred with petroleum ether and filtered off under suction. The product, obtained by chromatography over silica gel 60, 40–63 μm, using diisopropyl ether/ethanol, 3:2, was recrystallized from petroleum ether with activated charcoal.
Yield: 30% of theory
Melting point: 76° C.

Example 26

2-Dipropylamino-8-(2-butanesulphonamidoethoxy)-1,2,3,4-tetrahydronaphthalene

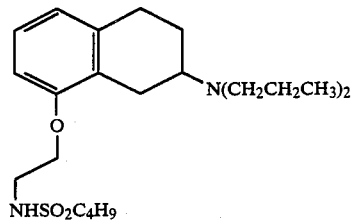

2.5 g (8.6 mmol) of 2-dipropylamino-8-(2-aminoethoxy)-1,2,3,4-tetrahydronaphthalene and 2.4 g (17.2 mmol) of potassium carbonate were initially introduced into 40 ml of toluene. 1.5 g (9.5 mmol) of butanesulphonyl chloride were added dropwise, and the mixture was then stirred for a further 2 h at room temperature. The mixture was then filtered and evaporated in a rotary evaporator. After chromatography on silica gel 60, 40–63 μm, using diisopropyl ether/ethanol, 3:2, the product was recrystallized from petroleum ether.
Yield: 27% of theory
$R_f$: 0.517

Example 27

2-Dipropylamino-8-(2-propionylamido-ethoxy)-1,2,3,4-tetrahydronaphthalene

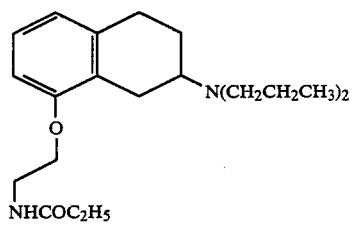

1.45 g (5 mmol) of 2-dipropylamino-8-(2-aminoethoxy)-1,2,3,4-tetrahydronaphthalene and 1.38 g (10 mmol) of potassium carbonate were initially introduced into 20 ml of toluene. 0.5 g (5.5 mmol) of propionyl chloride was 5 then added dropwise, and the mixture was subsequently stirred for 30 min under reflux. The mixture was then filtered and evaporated. The residue was stirred with N-hexane, and the product was filtered off under suction.
Yield: 75% of theory
Melting point: 67°–68° C.

Example 28

2-Dipropylamino-8-(2-ethoxycarbonylamido-ethoxy)1,2,3,4-tetrahydronaphthalene

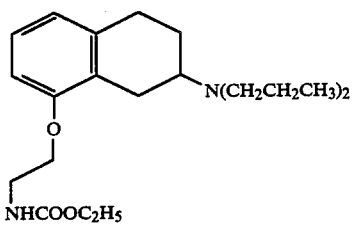

NHCOOC₂H₅

1.45 g (5 mmol) of 2-dipropylamino-8-(2-aminoethoxy)-1,2,3,4-tetrahydronaphthalene and 1.38 g (10 mmol) of potassium carbonate were initially introduced into 20 ml of toluene. 0.53 ml (5.5 mmol) of ethyl chloroformate was then added dropwise, and the mixture was stirred for a further 20 min at +25° C. The mixture was then filtered and evaporated. The product was obtained by chromatography over silica gel 60, 40–63 μm, using diisopropyl ether/ethanol, 3:2.

Yield: 71.8% of theory
$R_f$: 0.492

Example 29

2-Dipropylamino-8-[2-(3,3-diethylureido)-ethoxy]-1,2,3,4-tetrahydronaphthalene

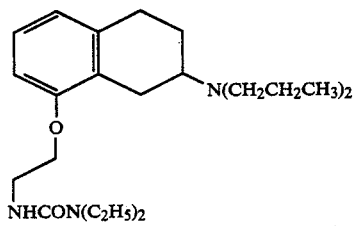

NHCON(C₂H₅)₂

1.45 g (5 mmol) of 2-dipropylamino-8-(2-aminoethoxy)-1,2,3,4-tetrahydronaphthalene and 1.38 g (10 mmol) of potassium carbonate were initially introduced into 20 ml of toluene. 0.77 g (5.5 mmol) of diethylcarbamoyl chloride was then added dropwise,. and the mixture was stirred for 2 h at +100° C. The mixture was then filtered and evaporated. The product was obtained by chromatography over silica gel 60, 40–63 μm, using diisopropyl ether/ethanol, 3:2.

Yield: 56.4% of theory
$R_f$: 0.408

Example 30

2-Dipropylamino-8-ureidoethoxy-1,2,3,4-tetrahydronaphthalene

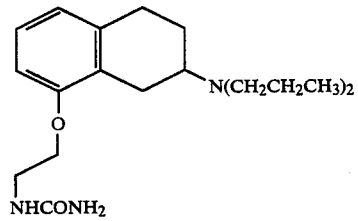

NHCONH₂

1.45 g (5 mmol) of 2-dipropylamino-8-(2-aminoethoxy)-1,2,3,4-tetrahydronaphthalene were dissolved in 10 ml of water and 10 ml of 1 N hydrochloric acid. A solution of 4.1 g (50 mmol) of potassium cyanate and 20 ml of water was then added dropwise at a temperature of +60° C. The mixture was stirred for 3 h at +60° C., the reaction product precipitating. This was filtered off under suction, and the residue was stirred with hot petroleum ether. After cooling, the product was filtered off under suction.

Yield: 83.8% of theory
Melting point: 107°–108° C.

Example 31

2-Dipropylamino-8-[2-(3-methylureido)ethoxy]1,2,3,4-tetrahydronaphthalene

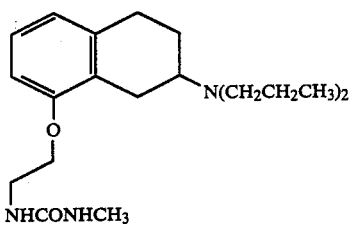

NHCONHCH₃

1.45 g (5 mmol) cf 2-dipropylamino-8-(2-aminoethoxy)-1,2,3,4-tetrahydronaphthalene were initially introduced into 20 ml of toluene. The reaction was catalyzed using 3 drops of triethylamine, and 0.325 ml (5.5 mmol) of methyl isocyanate was then added dropwise. The mixture was stirred for 1 h at +25° C. The mixture was evaporated, and the residue obtained was stirred with hot diisopropyl ether. The mixture was cooled, and the product was filtered off under suction.

Yield: 80.5% of theory
Melting point: 104°–105° C.

Example 32

2-Dipropylamino-8-[2-(3-butylureido)ethoxy]-1,2,3,4-tetrahydronaphthalene

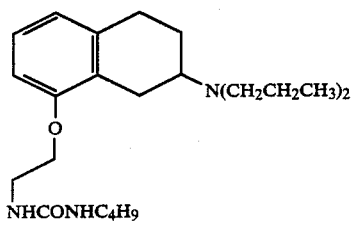

NHCONHC₄H₉

1.45 g (5 mmol) of 2-dipropylamino-8-(2-aminoethoxy)-1,2,3,4-tetrahydronaphthalene were initially introduced into 25 ml of toluene. The reaction was catalyzed using 3 drops of triethylamine, and 0.63 ml (5.5 mmol) of butyl isocyanate was then added dropwise. The mixture was stirred for 2 h at room temperature. The mixture was evaporated to dryness, and the residue was crystallized from petroleum ether/diisopropyl ether.

Yield: 82% of theory
Melting point: 90°–91° C.

Example 33

2-Dipropylamino-8-(2-formylamido-ethoxy)-1,2,3,4-tetrahydronaphthalene

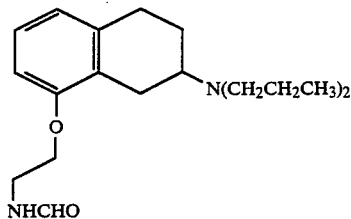

1.02 ml (10.8 mmol) of acetic anhydride and 0.86 ml (22.8 mmol) of formic acid were heated at +60° C. for 4 h. The mixture was then cooled to room temperature, and 1.45 g (5 mmol) of 2-dipropylamino-8-(2-aminoethoxy)-1,2,3,4-tetrahydronaphthalene were added dropwise. After the exothermic reaction had subsided, the mixture was then stirred for a further 2 h at room temperature. Ethyl acetate was then added, and the batch was adjusted to pH 11 using 1 molar sodium hydroxide solution. The aqueous phase was extracted a further time with ethyl acetate. The organic phases were combined, dried over sodium sulphate and evaporated. The residue was recrystallized from petroleum ether with activated charcoal.

Yield: 58.4% of theory
Melting point: 93° C.

Example 34

2-Dipropylamino-8-[2-(N,N-dimethylaminosulphonyl)-ethenyl]-1,2,3,4-tetrahydronaphthalene

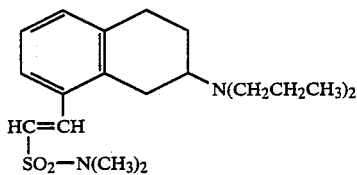

1.23 g (10 mmol) of dimethyl-methanesulphonamide and 150 mg (1 mmol) of benzyltriethylammonium chloride were stirred vigorously for 15 min at room temperature with 20 ml of 50% strength sodium hydroxide solution in 20 ml of methylene chloride. A solution of 7.8 g (30 mmol) of 2-dipropylamino-8-formyl-1,2,3,4-tetrahydronaphthalene in 5 ml of methylene chloride was subsequently added dropwise at room temperature, and the mixture was stirred overnight. The mixture was then diluted with plenty of water and extracted repeatedly with methylene chloride. The organic phase was dried over sodium sulphate and then evaporated. The product was obtained by chromatography over silica gel 60, 63–200 μm, using (a) cyclohexane/ethyl acetate/triethylamine, 80:19:1, and (b) cyclohexane/ethyl acetate/triethylamine, 50:49:1.

Yield: 50.7% of theory
$R_f$: 0.617 (diisopropyl ether: ethanol 3:2)

Example 35

2-Dipropylamino-8-[2-(N,N-dimethylaminosulphonyl)-ethyl]-1,2,3,4-tetrahydronaphthalene

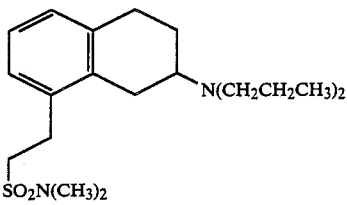

320 mg (8 mmol) of lithium aluminum hydride were initially introduced into 20 ml of absolute diethyl ether under argon. A solution of 1.46 g (4 mmol) of 2-diisopropylamino -8-[2-(N,N-dimethylaminosulphonyl)ethenyl]-1,2,3,4-tetrahydronaphthalene in 10 ml of absolute diethyl ether was then added dropwise. The mixture was stirred for 2.5 h under reflux. Decomposition was then carefully effected with water, and the residue was filtered off under suction and washed thoroughly with ethyl acetate. The phases were then separated and the organic phase was dried over sodium sulphate and then evaporated. The product was recrystallized from isopropanol/water, filtered off under suction and dried at +50° C. in a high vacuum.

Yield: 55.2% of theory
Melting point: 84° C.

Example 36

2-Dipropylamino-8-(2-nitro-ethenyl)-1,2,3,4-tetrahydronaphthalene

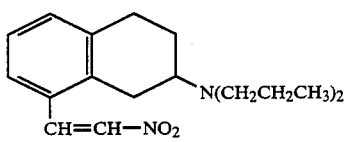

14 g (54 mmol) of 2-dipropylamino-8-formyl-1,2,3,4-tetrahydronaphthalene, 14 ml of nitromethane and 5.6 g (73 mmol) of ammonium acetate were stirred for 2 h under reflux in 56 ml of glacial acetic acid. After cooling, the mixture was adjusted to pH 12 using 5 molar sodium hydroxide solution and extracted 3 times with ethyl acetate. The organic phase was dried using sodium sulphate and then evaporated. The product was obtained by chromatography over silica gel 60, 63–200 μm, using diisopropyl ether/triethylamine, 99.5:0.5.

Yield: 52.1% of theory
$^1$H-NMR (300 MHz, CDCl$_3$): protons of the nitro-ethylene radical:

$\delta = 7.38$ ppm; $J = 15$ Hz, 1 H, $\delta = 8.25$ ppm; $J = 15$ Hz, 1 H.

Example 37

2-Dipropylamino-8-(2-amino-ethyl)-1,2,3,4,-tetrahydronaphthalene

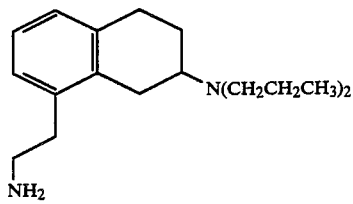

820 mg (20.4 mmol) of sodium borohydride were initially introduced into 30 ml of absolute tetrahydrofuran at 0° C. under nitrogen. 3.24 ml (25.8 mmol) of boron trifluoride diethyl ether complex were added dropwise at this temperature, and the mixture was subsequently stirred for 15 minutes at room temperature. A solution of 1.3 g (4.3 mmol) of 2-dipropylamino-8-(2-nitro-ethenyl)-1,2,3,4-tetrahydronaphthalene and 10 ml of absolute tetrahydrofuran was then added dropwise, and the mixture was then stirred for 5.5 h under reflux. After cooling to room temperature, 55 ml of ice water were carefully added dropwise, and the mixture was then acidified using 55 ml of 1 N hydrochloric acid. The mixture was subsequently stirred for 2 h at +80°–+85° C. The cooled aqueous phase was washed twice with 35 ml of ether, then adjusted to pH 12 using 5 molar sodium hydroxide solution, and the product was extracted with methylene chloride. The extract was dried over sodium sulphate and evaporated. The product was obtained by subsequent chromatography over silica gel 60, 40–63 μm, using isopropanol/triethylamine, 95:5.

Yield: 50.8% of theory
$R_f$: 0.192

Example 38

2-Dipropylamino-8-(2-methanesulphonamido-ethyl)-1,2,3,4-tetrahydronaphthalene hydrochloride

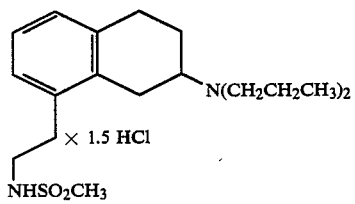

1.2 g (4.4 mmol) of 2-dipropylamino-8-(2-aminoethyl)-1,2,3,4-tetrahydronaphthalene and 1.21 g (8.8 mmol) of potassium carbonate were initially introduced into 20 ml of methylene chloride. 550 mg (4.8 mmol) of methanesulphonyl chloride were then added dropwise at 25° C. The mixture was stirred overnight at room temperature. The mixture was then filtered, and the filtrate was washed once with water, dried over sodium sulphate and evaporated. Diethyl ether was added to the residue, methylene chloride was added until everything was dissolved, and the hydrochloride was precipitated using ethereal hydrochloric acid. The product was filtered off under suction and dried at 40° C. in a high vacuum.

Yield: 56.2% of theory
Melting point: 212° C. (decomp.)

Example 39

2-Dipropylamino-8-(2-butanesulphonamido-ethyl)-1,2,3,4-tetrahydronaphthalene

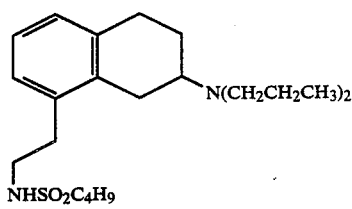

1.1 g (4 mmol) of 2-dipropylamino-8-(2-amino-ethyl)-1,2,3,4-tetrahydronaphthalene and 1.1 g (8 mmol) of potassium carbonate were initially introduced into 20 ml of methylene chloride. 690 mg (4.4 mmol) of butanesulphonyl chloride were then added dropwise, and the mixture was stirred for 5.5 h at room temperature. 20 ml of water were then added, and the mixture was stirred vigorously for 10 min. The phases were separated, and the aqueous phases were extracted once more with methylene chloride. The organic phases were combined, dried over sodium sulphate and then evaporated. The product was obtained by chromatography over silica gel 60, 40–63 μm, using ethyl acetate.

Yield: 72.9% of theory
$R_f$: 0.592 (diisopropyl ether : ethanol 3:2)

Example 40

2-Dipropylamino-8-[2-(p-chlorobenzenesulphonamido)-ethyl]-1,2,3,4-tetrahydronaphthalene

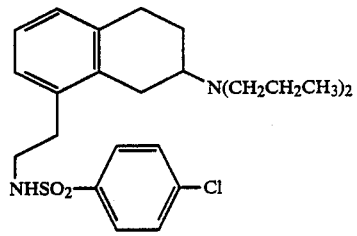

1.1 g (4 mmol) of 2-dipropylamino-8-(2-amino-ethyl)1,2,3,4-tetrahydronaphthalene were initially introduced into 15 ml of methylene chloride with 2 ml of 50% strength potassium carbonate solution. A solution of 930 mg (4.4 mmol) of p-chlorobenzenesulphonyl chloride in 15 ml of methylene chloride was then added dropwise with vigorous stirring. The mixture was stirred for 1 h at room temperature. 20 ml of water were added, and the mixture was stirred vigorously. The phases were separated, and the aqueous phase was extracted once more with methylene chloride. The organic phases were combined, dried over sodium sulphate and evaporated. The product was obtained by chromatography over silica gel 60, 40–63 μm, using ethyl acetate.

Yield: 97.4% of theory
$R_f$: 0.650 (diisopropyl ether : ethanol 3:2)

Example 41

2-Dipropylamino-8-(2-ethoxycarbonylamido-ethyl)-1,2,3,4-tetrahydronaphthalene

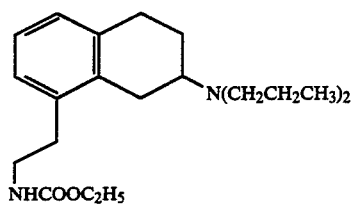

1.1 g (4 mmol) of 2-dipropylamino-8-(2-amino-ethyl)-1,2,3,4-tetrahydronaphthalene and 1.1 g (8 mmol) of potassium carbonate were initially introduced into 20 ml of methylene chloride. 0.45 ml (4.4 mmol) of ethyl chloroformate was then added dropwise at +25° C., and the mixture was stirred for a further 1 h at room temperature. 20 ml of water were then added, and the mixture was stirred vigorously for 10 min. The phases were separated, and the aqueous phase was extracted once more with methylene chloride. The organic phases were combined, dried over sodium sulphate and then evaporated. The residue was then dissolved in 30 ml of 3 N hydrochloric acid, extracted 3 times with diethyl ether, and again adjusted to pH 12, and the product was extracted with ethyl acetate, dried over sodium sulphate and evaporated.

Yield: 85.8% of theory $R_f$: 0.598 (diisopropyl ether : ethanol 3:2)

Example 42

2-Dipropylamino-8-(2-benzyloxycarbonylamido-ethyl)-2,3,4-tetrahydronaphthalene

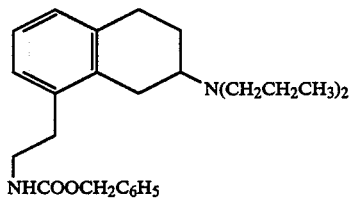

3.5 g (12.75 mmol) of 2-dipropylamino-8-(2-aminoethyl)-1,2,3,4-tetrahydronaphthalene and 3.5 g (25.5 mmol) of potassium carbonate were initially introduced into 50 ml of methylene chloride. 4.7 ml (14 mmol) of benzyl chloroformate (50% strength solution in toluene) were then added dropwise at 25° C., and the mixture was stirred for a further 2 h at room temperature. 50 ml of water were subsequently added, and the mixture was stirred vigorously for 10 min. The phases were separated, and the aqueous phase was extracted once more with methylene chloride. The organic phases were combined, dried over sodium sulphate and then evaporated. The product was obtained by chromatography over silica gel 60, 40–63 μm, using ethyl acetate.

Yield: 92.1% of theory $R_f$: 0.567 (diisopropyl ether : ethanol 3:2)

Example 43

2-Dipropylamino-8-(2-ureido-ethyl)-1,2,3,4-tetrahydronaphthalene

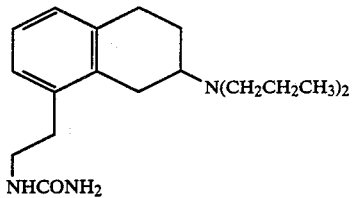

1.1 g (4 mmol) of 2-dipropylamino-8-(2-aminoethyl)-1,2,3,4-tetrahydronaphthalene were dissolved in 8 ml of water and 8 ml of 1 N hydrochloric acid, and heated to +60° C. A solution of 3.24 g (40 mmol) of potassium cyanate and 15 ml of water was added dropwise at this temperature. The mixture was stirred for 1 h at +60° C. The mixture was then cooled and filtered under suction. The product was recrystallized from petroleum ether/diisopropyl ether with activated charcoal.

Yield: 43.4% of theory

Melting point: 123°–124° C.

Example 44

2-Dipropylamino-8-[2-(3-methylureido)ethyl]-1,2,3,4-tetrahydronaphthalene

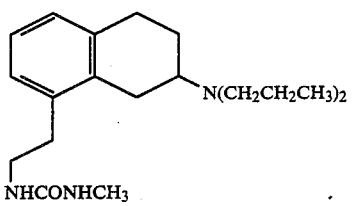

1.3 g (4.7 mmol) of 2-dipropylamino-8-(2-aminoethyl)-1,2,3,4-tetrahydronaphthalene were initially introduced into 20 ml of toluene. The reaction was catalyzed using 3 drops of triethylamine, and 0.31 ml (5.17 mmol) of methyl isocyanate were then added dropwise. The mixture was stirred overnight at room temperature, and then evaporated. After subsequent chromatography over silica gel 60, 40–63 μm, using diisopropyl ether/ethanol/triethylamine, the product was stirred with petroleum ether and a little diisopropyl ether, and filtered off under suction.

Yield: 21.1% of theory

Melting point: 70° C.

Example 45

2-Dipropylamino-8-(2-formylamido-ethyl)-1,2,3,4-tetrahydronaphthalene

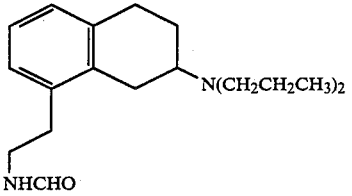

1.02 ml (10.8 mmol) of acetic anhydride and 0.86 ml (22.8 mmol) of formic acid were heated at +50°–+60° C. for 4 h. The mixture was cooled to room temperature, and 1.4 g (5 mmol) of 2-dipropylamino-8-(2-aminoethyl)-1,2,3,4-tetrahydronaphthalene were then added dropwise, the temperature being maintained below +40° C. during this addition. The mixture was subsequently stirred for 2 h at room temperature. The mixture was then adjusted to pH 12 using 5 molar sodium hydroxide solution and extracted with methylene chloride. The extract was dried over sodium sulphate and then evaporated. The product was obtained by chromatography over silica gel 6, 40–63 μm, using diisopropyl ether/ethanol 3:2.

Yield: 56.3% of theory $R_f$: 0.242

(All TLCs were carried out on TLC aluminum foils, silica gel 60, F254, 5×7.5 cm, run height 6 cm).

Example 46

2-Dipropylamino-8-[2-(N-methylaminosulphonyl)ethenyl]1,2,3,4-tetrahydronaphthalene

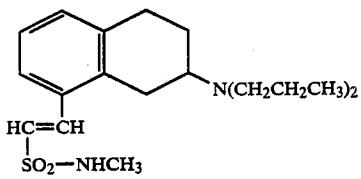

This compound was prepared analogously to Example 34. N-methyl-methane sulphonamide was employed as the starting material.

Yield: 49.6% of theory $R_f$: 0.383 (diisopropyl ether: ethanol 3:2)

Example 47

2-Dipropylamino-8-[2-(N-methylaminosulphonyl)ethyl]-1,2,3,4-tetrahydronaphthalene

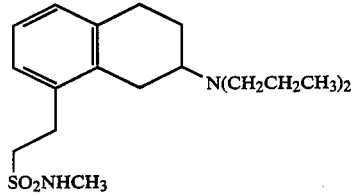

This compound was prepared analogously to Example 35 by reduction of the compound of Example 47 using lithium aluminum hydride.

Yield: 33% of theory $R_f$: 0.492 (diisopropyl ether: ethanol 3:2)

Example 48

2-Dipropylamino-8-[2-(2-naphthyl)sulphonamidoethyl]-1,2,3,4-tetrahydronaphthalene

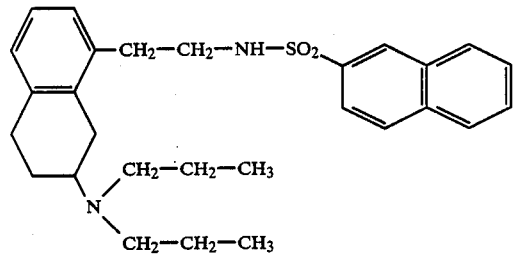

961 mg (3.5 mmol) of 2-dipropylamino-8-(2-aminoethyl)-1,2,3,4-tetrahydronaphthalene were introduced into 15 ml of methylene chloride containing 1.75 ml of 50% strength potassium carbonate solution. A solution of 873 mg (3.85 mmol) of naphthalene-2-sulphonyl chloride and 5 ml of methylene chloride was added dropwise and the mixture was stirred at room temperature for a further 20 hours. The mixture was then diluted with water and methylene chloride. The organic phase was separated off, dried over sodium sulphate and concentrated. The residue was subsequently chromatographed using cyclohexane/ethyl acetate 1:1 over silica gel 60, 40–63 μm.

Yield: 1.32 g=81.2% of theory

Rf: 0.117 (cyclohexane: ethyl acetate 1:1)

Example 49

2-Dipropylamino-8-[2-(3,4-dichlorophenyl)-sulphonamido-ethyl]-1,2,3,4-tetrahydronaphthalene

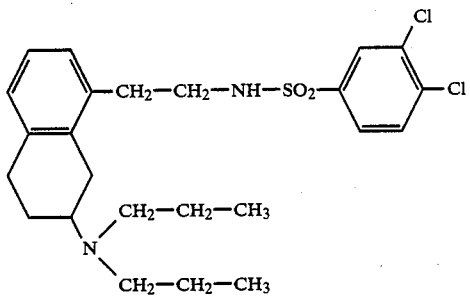

500 mg (1.82 mmol) of 2-dipropylamino-8-(2-aminoethyl)-1,2,3,4-tetrahydronaphthalene were introduced into 10 ml of methylene chloride containing 1 ml of 50% strength potassium carbonate solution. A solution of 491 mg (2.0 mmol) of 3,4-dichlorobenzenesulphonyl chloride and 5 ml of methylene chloride was added dropwise, and the mixture was stirred at room temperature for a further 2 hours. The mixture was then diluted with water and methylene chloride. The organic phase was separated off, dried over sodium sulphate and concentrated. The residue was subsequently chromatographed using cyclohexane/ethyl acetate 1:1 over silica gel 60, 40–63 μm.

Yield: 3.82 mg=43.4% of theory

Rf: 0.121 (cyclohexane:ethyl acetate 1:1)

Example 50

2-Dipropylamino-8-[2-N-(4-N-saccharinyl)-n-butylaminoethyl]-1,2,3,4-tetrahydronaphthalene hydrochloride

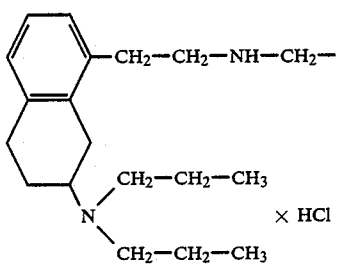

1.3 g (4.7 mmol) of 2-dipropylamino-8-(2-aminoethyl)-1,2,3,4-tetrahydronaphthalene and 1.38 g (10 mmol of potassium carbonate were introduced into 10 ml of dimethylformamide. A solution of 1.49 g (4.7 mmol) of 4-N-saccharinyl-n-butyl bromide and 5 ml of dimethylformamide was added dropwise, and the mixture was stirred at 80° C. for a further 5 hours. The mixture was subsequently poured into water and extracted with ethyl acetate. The extracts were chromatographed twice with ethyl acetate and once with cyclohexane:ethyl acetate:triethylamine 50:49:1 over silica gel, 40–63 μm. The viscous oil was dissolved in ether, ethereal hydrochloric acid was added, and the mixture was concentrated and dried at 50° C. in a high vacuum.

Yield: 300 mg = 11.6% of theory
Rf: 0.612 (methanol:triethylamine 95+5)

USE EXAMPLES

Example 51

(A) Affinity to the 5-HT$_1$ Receptor

In Table 1, as an example, the high affinity of the compounds according to the invention to 5-hydroxytryptamine receptors of the sub-type 1 is shown. The values specified are data which were determined from receptor binding studies using calf hippocampus membrane preparations. 3 H-serotonin was used for this purpose as radioactively labelled ligand.

TABLE 1

| Compound of Example No. | Ki (nmol/l) |
|---|---|
| 1 | 20 |
| 2 | 13 |
| 6 | 7 |
| 25 | 13 |
| 26 | 17 |
| 28 | 4 |
| 30 | 30 |
| 33 | 19 |
| 42 | 5 |

Comparison

In this test model, the compounds described in EP-A1- 41 488 with $R^1$=OCH$_3$, $R^2$=$R^3$=nC$_3$H$_7$ and $R^1$=OH, $R^2$=$R^3$=nC$_3$H$_7$ exhibit Ki values of 3 and 2 nmol/l respectively.

(B) Investigations of the Serotonin-Agonistic/Antagonistic Action

To this purpose, the action on the contraction, caused by serotonin, of the arteria basilaris of the dog is investigated [cf. Peroutka et al., Brain Research 259, 327 (1983)].

TABLE 2

| Compound of Example No. | Effect Antagonistic |
|---|---|
| 1 | − |
| 2 | − |
| 25 | + |
| 28 | − |
| 30 | + |
| 33 | + |

Comparison from EP-Al- 41 488:
$R^1$ = OH, $R^2$ = nC$_3$H$_7$, $R^3$ = nC$_3$H$_7$ It will be understood that the specification and examples are illustrative but not limitative of the present invention and that other embodiments within the spirit and scope of the invention will suggest themselves to those skilled in the art.

We claim:
1. An 8-substituted 2-aminotetralin of the formula

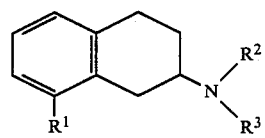

in which
$R^1$ represents —(CH$_2$)$_a$—X, —O—(CH$_2$)$_a$—X or —CH=CH—(CH$_2$)$_b$—X,
a denotes a number 1 to 10,
b denotes a number 0 to 8, and
X denotes a group of the formula —NR$^{12}$R$^{13}$, —COR$^{14}$, —SO$_2$R$^{15}$ or —OR$^{16}$, wherein
R$^{12}$ and R$^{13}$ are identical or different and represent hydrogen, alkyl, aryl or aralkyl, where the aryl radicals may be substituted by halogen, cyano, alkyl, alkoxy or trifluoromethyl, or represent a group of the formula —COR$^{14}$, —SO$_2$R$^{15}$ or —(CH$_2$)$_c$—NR$^{12}$R$^{13}$,
R$^{14}$ denotes hydrogen, or denotes an —NHR$^{17}$ group, or denotes alkyl or alkoxy, or denotes aryl, aryloxy, aralkyl, aralkoxy or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino,
R$^{15}$ denotes cycloalkyl, or denotes alkyl which may be substituted by cyano, halogen, trifluoromethyl, trifluoromethoxy or alkoxycarbonyl, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, or denotes an —NR$^{10}$R$^{11}$ group, where R$^{10}$ and R$^{11}$ have the abovementioned meaning, R$^{16}$ denotes hydrogen, alkyl, aryl, aralkyl, or a group of the formula CONR$^{10}$R$^{11}$ R$^{17}$ denotes hydrogen, or denotes cycloalkyl, or denotes alkyl which is optionally substituted by cyano, halogen, trifluoromethyl or trifluoromethoxy, or denotes aryl, aralkyl or heteroaryl, where the radicals mentioned may be up to trisubstituted, identically or differently, by alkyl, alkoxy, alkylthio, halogen, cyano, trifluoromethyl, trifluoromethoxy, trifluoromethylthio, amino, alkylamino or dialkylamino, and c denotes a number 1 to 8, or where R$^{12}$ and R$^{13}$, together with the nitrogen atom, form a ring from the series comprising wherein n denotes a number 1 or 2, and A represents hydrogen or cycloalkyl, or represents alkyl which may be substituted by halogen, hydroxyl, amino, alkylamino, dialkylamino, carbamoyl or sulphamoyl, or represents aryl, heteroaryl, aralkyl, alkoxycarbonyl, alkylsulphonyl, phenylsulphonyl, tolylsulphonyl, benzylsulphonyl, formyl, carbamoyl or sulphamoyl, R$^2$ represents hydrogen or alkyl, and R$^3$ represents alkyl.

2. An 8-substituted 2-aminotetralin or salt thereof according to claim 1, in which R$^1$ represents —(CH$_2$)$_a$—X, —O—(CH$_2$)$_a$—X or —CH=CH—(CH$_2$)$_b$—X, a denotes a number 1 to 8, b denotes a number 0 to 6, and X denotes a group of the formula —NR$^{12}$R$^{13}$, —COR$^{14}$, —SO$_2$R$^{15}$ or —OR$^{16}$, where R$^{12}$ and R$^{13}$ are identical or different and represent hydrogen, lower alkyl, phenyl or benzyl, where the radicals mentioned may be substituted by fluorine, chlorine, bromine, lower alkyl, lower alkoxy or trifluoromethyl, or represent a group of the formula —COR$^{14}$, —SO$_2$R$^{15}$ or —(CH$_2$)$_c$—NR$^{12}$R$^{13}$, R$^{14}$ denotes an —NHR$^{17}$ group, or denotes lower alkyl or lower alkoxy, or denotes phenyl, benzyl, benzyloxy, thienyl, furyl, pyridyl, pyrimidyl, quinolyl, isoquinolyl, benzothiazolyl, benzoxazolyl, thiazolyl, oxazolyl, isoxazolyl or isothiazolyl, which are optionally substituted by lower alkyl, lower alkoxy, fluorine, chlorine bromine, trifluoromethyl, dimethylamino or diethylamino, R$^{15}$ denotes cyclopropyl, cyclopentyl, cyclohexyl, or lower alkyl which is optionally substituted by cyano, fluorine, chlorine, bromine, trifluoromethyl or lower alkoxycarbonyl, or denotes phenyl, naphthyl, benzyl, thienyl, furyl, pyrimidyl, pyridyl, quinolyl, isoquinolyl, benzothiazolyl, benzoxazolyl, thiazolyl, oxazolyl, isoxazolyl or isothiazolyl, which are optionally monosubstituted or polysubstituted by lower alkyl, lower alkoxy, fluorine, chlorine, bromine, trifluoromethyl, dimethylamino or diethylamino, the substituents being identical or different or denotes an —NR$^{10}$R$^{11}$ group, where R$^{10}$ and R$^{11}$ have the abovementioned meaning, R$^{16}$ denotes hydrogen, lower alkyl, phenyl or benzyl, R$^{17}$ denotes hydrogen, or lower alkyl which is optionally substituted by cyano, fluorine, chlorine or bromine, or phenyl, benzyl, thienyl, furyl, pyridyl, pyrimidyl, quinolyl, isoquinolyl, benzothiazolyl, benzoxazolyl, thiazolyl, oxazolyl, isoxazolyl or isothiazolyl which are optionally substituted by lower alkyl, lower alkoxy, fluorine, chlorine, bromine, trifluoromethyl, dimethylamino or diethylamino, and c denotes number 1 to 6, or where R$^{12}$ and R$^{13}$, together with the nitrogen atom, form a ring from the series comprising

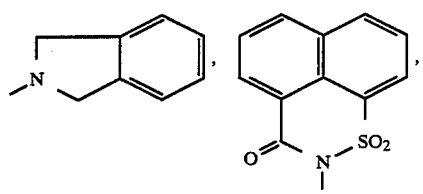

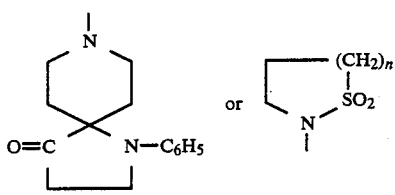

wherein
n denotes a number 1 or 2,
R² represents hydrogen or lower alkyl and
R³ represents lower alkyl.

3. An 8-substituted 2-aminotetralin or salt thereof according to claim 1, in which
R¹ represents —(CH₂)ₐ—X, —O—(CH₂)ₐ—X or —CH=CH—(CH₂)ᵦ—X,
a denotes a number 1 to 6,
b denotes a number 0 to 4, and
X denotes a group of the formula —NR¹²R¹³, —COR¹⁴, —SO₂R¹⁵ or —OR¹⁶, where
R¹² and R¹³ are identical or different and represent hydrogen, methyl, ethyl, propyl, isopropyl, butyl, isobutyl, or represent phenyl which is optionally substituted by fluorine, chlorine, methyl or methoxy, or represent a —COR¹⁴, —SO₂R¹⁵ or

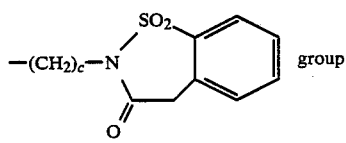 group

R¹⁴ denotes hydrogen, or denotes an —NHR¹⁷ group, or denotes methyl, ethyl, propyl, isopropyl, methoxy, ethoxy, propoxy, isopropoxy, or denotes phenyl, benzyl, benzyloxy, thienyl, furyl, pyridyl, pyrimidyl, quinolyl or isoquinolyl which are optionally substituted by methyl, methoxy, fluorine or chlorine,
R¹⁵ denotes methyl, ethyl, propyl, isopropyl, butyl or isobutyl which are optionally substituted by fluorine, chlorine, methoxycarbonyl, ethoxycarbonyl, propoxycarbonyl, isopropoxycarbonyl, butoxycarbonyl or isobutoxycarbonyl, or denotes phenyl, naphthyl, thienyl, furyl, pyridyl, pyrimidyl, quinolyl or isoquinolyl which are optionally monosubstituted or polysubstituted by methyl, ethyl, propyl, isopropyl methoxy, fluorine or chlorine, the substituents being identical or different, or denotes an NR¹⁰R¹¹ group.
R¹⁶ denotes hydrogen, methyl, ethyl, propyl, isopropyl, phenyl or benzyl,
R¹⁷ denotes hydrogen, or denotes methyl, ethyl, propyl, isopropyl, butyl, isobutyl, pentyl, isopentyl, hexyl or isohexyl which are optionally substituted by fluorine or chlorine, or denotes phenyl which may be substituted by fluorine, chlorine, methyl or methoxy, and
n denotes a number 1 to 4,
R² represents hydrogen, methyl, ethyl, propyl or isopropyl, and
R³ represents methyl, ethyl, propyl or isopropyl.

4. An 8-substituted 2-aminotetralin or salt thereof according to claim 1, in which
R¹ represents —(CH₂)ₐ—X, —O—(CH₂)ₐ—X or —CH=CH—(CH₂)ᵦ—X,
a denotes a number 1 to 4,
b denotes a number 0 to 2, and
X denotes a group of the formula —NR¹²R¹³, —COR⁴, —SO₂R¹⁵ or —OR¹⁶, where
R¹² and R¹³ are identical or different and represent hydrogen, methyl, ethyl or propyl, or represent a —COR¹⁴, —SO₂R¹⁵ or

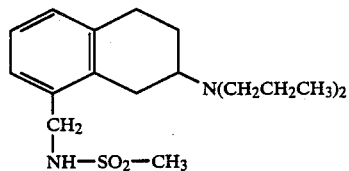 group,

R¹⁴ denotes hydrogen, or denotes an —NHR¹⁴ group, or denotes methyl, ethyl, propyl, methoxy or ethoxy,
R¹⁵ denotes trifluoromethyl, methyl, ethyl, propyl, isopropyl, butyl or isobutyl, or denotes phenyl or naphthyl which are optionally monosubstituted or polysubstituted by methyl or chlorine, or denotes an —NR¹⁰R¹¹ group,
R¹⁶ denotes hydrogen, methyl, ethyl or propyl,
R¹⁷ denotes hydrogen, or denotes methyl, ethyl, propyl, isopropyl, butyl or isobutyl, or denotes phenyl, and
c denotes a number 2 to 4, and
R² and R³ represent propyl.

5. A compound according to claim 1, wherein such compound is 2-dipropylamino-8-methylsulphonamidomethyl-1-tetrahydronaphthalene of the formula 6. A composition suitable for treating a disorder of the central nervous system, the cardiovascular system or the intestinal tract comprising an amount effective therefor of a compound or salt thereof according to claim 1 and a diluent.

7. A unit dose of a composition according to claim 6 in the form of a tablet, capsule or ampule.

8. A method of treating a disorder of the central nervous system, the cardiovascular system or the intestinal tract comprising administering to a patient suffering therefrom an amount effective therefor of a compound or salt thereof according to claim 1.

* * * * *

UNITED STATES PATENT AND TRADEMARK OFFICE
CERTIFICATE OF CORRECTION

PATENT NO. : 4,968,679

DATED : November 6, 1990

INVENTOR(S) : Junge et al.

It is certified that error appears in the above-identified patent and that said Letters Patent is hereby corrected as shown below:

Col. 72, line 2     After " alkyl " insert -- or a salt thereof --

Col. 74, line 41    After " -1 " insert -- ,2,3,4 --

Signed and Sealed this

Tenth Day of November, 1992

Attest:

DOUGLAS B. COMER

*Attesting Officer*    *Acting Commissioner of Patents and Trademarks*